(12) United States Patent
Alberts et al.

(10) Patent No.: US 9,776,003 B2
(45) Date of Patent: Oct. 3, 2017

(54) REVERSING COGNITIVE-MOTOR IMPAIRMENTS IN PATIENTS HAVING A NEURO-DEGENERATIVE DISEASE USING A COMPUTATIONAL MODELING APPROACH TO DEEP BRAIN STIMULATION PROGRAMMING

(71) Applicant: The Cleveland Clinic Foundation, Cleveland, OH (US)

(72) Inventors: Jay L. Alberts, Chagrin Falls, OH (US); Cameron C. McIntyre, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 15/148,996

(22) Filed: May 6, 2016

(65) Prior Publication Data
US 2016/0250473 A1 Sep. 1, 2016

Related U.S. Application Data

(63) Continuation of application No. 12/986,735, filed on Jan. 7, 2011, now abandoned, which is a
(Continued)

(51) Int. Cl.
*A61N 1/00* (2006.01)
*A61N 1/36* (2006.01)
*A61N 1/05* (2006.01)

(52) U.S. Cl.
CPC ....... *A61N 1/36103* (2013.01); *A61N 1/0534* (2013.01); *A61N 1/36067* (2013.01); *A61N 1/36135* (2013.01)

(58) Field of Classification Search
CPC .............. A61N 1/36103; A61N 1/0534; A61N 1/36067; A61N 1/36135
See application file for complete search history.

(56) References Cited

U.S. PATENT DOCUMENTS 3,999,555 A 12/1976 Person
4,144,889 A 3/1979 Tyers et al.
(Continued)

FOREIGN PATENT DOCUMENTS

EP 1048320 11/2000
EP 1166819 1/2002
(Continued)

OTHER PUBLICATIONS

Alberts et al., "Bilateral subthalamic stimulation impairs cognitive-motor performance in Parkinson's disease patients", Brain (2008),131,3348-3360.*
(Continued)

*Primary Examiner* — Mallika D Fairchild
(74) *Attorney, Agent, or Firm* — Lowe Graham Jones PLLC; Bruce E. Black

(57) ABSTRACT

A system and method may provide for conducting a stimulation of anatomic regions to treat a neuromotor, neurocognitive or neuromotor and neurocognitive disorder, according to which stimulation, motor regions are stimulated, while creep of current to non-motor regions is minimized. Stimulation parameters may be selected based on tests of motor function, tests of cognitive function, and tests of a combination of motor and cognitive functions.

20 Claims, 7 Drawing Sheets

Related U.S. Application Data continuation-in-part of application No. PCT/US2010/058770, filed on Dec. 2, 2010.

(60) Provisional application No. 61/265,782, filed on Dec. 2, 2009.

(56) References Cited

U.S. PATENT DOCUMENTS

| | | |
|---|---|---|
| 4,177,818 A | 12/1979 | De Pedro |
| 4,341,221 A | 7/1982 | Testerman |
| 4,378,797 A | 4/1983 | Osterholm |
| 4,445,500 A | 5/1984 | Osterholm |
| 4,735,208 A | 4/1988 | Wyler et al. |
| 4,765,341 A | 8/1988 | Mower et al. |
| 4,841,973 A | 6/1989 | Stecker |
| 5,067,495 A | 11/1991 | Brehm |
| 5,222,494 A | 6/1993 | Baker, Jr. |
| 5,255,693 A | 10/1993 | Dutcher |
| 5,259,387 A | 11/1993 | dePinto |
| 5,304,206 A | 4/1994 | Baker, Jr. et al. |
| 5,344,438 A | 9/1994 | Testerman et al. |
| 5,560,360 A | 10/1996 | Filler et al. |
| 5,565,949 A | 10/1996 | Kasha, Jr. |
| 5,593,427 A | 1/1997 | Gliner et al. |
| 5,601,612 A | 2/1997 | Gliner et al. |
| 5,607,454 A | 3/1997 | Cameron et al. |
| 5,620,470 A | 4/1997 | Gliner et al. |
| 5,651,767 A | 7/1997 | Schulmann |
| 5,711,316 A | 1/1998 | Elsberry et al. |
| 5,713,922 A | 2/1998 | King |
| 5,716,377 A | 2/1998 | Rise et al. |
| 5,749,904 A | 5/1998 | Gliner et al. |
| 5,749,905 A | 5/1998 | Gliner et al. |
| 5,776,170 A | 7/1998 | MacDonald et al. |
| 5,843,148 A | 12/1998 | Gijsbers et al. |
| 5,859,922 A | 1/1999 | Hoffmann |
| 5,868,740 A | 2/1999 | LeVeen et al. |
| 5,897,583 A | 4/1999 | Meyer et al. |
| 5,910,804 A | 6/1999 | Fortenbery et al. |
| 5,925,070 A | 7/1999 | King et al. |
| 5,938,690 A | 8/1999 | Law et al. |
| 5,978,713 A | 11/1999 | Prutchi et al. |
| 6,016,449 A | 1/2000 | Fischell et al. |
| 6,029,090 A | 2/2000 | Herbst |
| 6,029,091 A | 2/2000 | de la Rama et al. |
| 6,050,992 A | 4/2000 | Nichols |
| 6,058,331 A | 5/2000 | King |
| 6,094,598 A | 7/2000 | Elsberry et al. |
| 6,096,756 A | 8/2000 | Crain et al. |
| 6,109,269 A | 8/2000 | Rise et al. |
| 6,128,538 A | 10/2000 | Fischell et al. |
| 6,129,685 A | 10/2000 | Howard, III |
| 6,146,390 A | 11/2000 | Heilbrun et al. |
| 6,161,044 A | 12/2000 | Silverstone |
| 6,167,311 A | 12/2000 | Rezai |
| 6,181,969 B1 | 1/2001 | Gord |
| 6,192,266 B1 | 2/2001 | Dupree et al. |
| 6,205,361 B1 | 3/2001 | Kuzma |
| 6,208,881 B1 | 3/2001 | Champeau |
| 6,246,912 B1 | 6/2001 | Sluijter et al. |
| 6,253,109 B1 | 6/2001 | Gielen |
| 6,301,492 B1 | 10/2001 | Zonenshayn |
| 6,336,899 B1 | 1/2002 | Yamazaki |
| 6,343,226 B1 | 1/2002 | Sunde et al. |
| 6,353,762 B1 | 3/2002 | Baudino et al. |
| 6,366,813 B1 | 4/2002 | Dilorenzo |
| 6,368,331 B1 | 4/2002 | Front et al. |
| 6,393,325 B1 | 5/2002 | Mann et al. |
| 6,421,566 B1 | 7/2002 | Holsheimer |
| 6,435,878 B1 | 8/2002 | Reynolds et al. |
| 6,442,432 B2 | 8/2002 | Lee |
| 6,494,831 B1 | 12/2002 | Koritzinsky |
| 6,507,759 B1 | 1/2003 | Prutchi et al. |
| 6,510,347 B2 | 1/2003 | Borkan |
| 6,516,227 B1 | 2/2003 | Meadows et al. |
| 6,517,480 B1 | 2/2003 | Krass |
| 6,560,490 B2 | 5/2003 | Grill et al. |
| 6,579,280 B1 | 6/2003 | Kovach et al. |
| 6,600,956 B2 | 7/2003 | Maschino et al. |
| 6,606,523 B1 | 8/2003 | Jenkins |
| 6,609,029 B1 | 8/2003 | Mann et al. |
| 6,609,031 B1 | 8/2003 | Law et al. |
| 6,609,032 B1 | 8/2003 | Woods et al. |
| 6,631,297 B1 | 10/2003 | Mo |
| 6,654,642 B2 | 11/2003 | North et al. |
| 6,662,053 B2 | 12/2003 | Borkan |
| 6,675,046 B2 | 1/2004 | Holsheimer |
| 6,684,106 B2 | 1/2004 | Herbst |
| 6,687,392 B2 | 2/2004 | Touzawa et al. |
| 6,690,974 B2 | 2/2004 | Archer et al. |
| 6,692,315 B1 | 2/2004 | Soumillion et al. |
| 6,708,096 B1 | 3/2004 | Frei et al. |
| 6,741,892 B1 | 5/2004 | Meadows et al. |
| 6,748,276 B1 | 6/2004 | Daignault, Jr. et al. |
| 6,778,846 B1 | 8/2004 | Martinez et al. |
| 6,845,267 B2 | 1/2005 | Harrison et al. |
| 6,850,802 B2 | 2/2005 | Holsheimer |
| 6,895,280 B2 | 5/2005 | Meadows et al. |
| 6,937,891 B2 | 8/2005 | Leinders et al. |
| 6,937,903 B2 | 8/2005 | Schuler et al. |
| 6,944,497 B2 | 9/2005 | Stypulkowski |
| 6,944,501 B1 | 9/2005 | Pless |
| 6,950,707 B2 | 9/2005 | Whitehurst |
| 6,969,388 B2 | 11/2005 | Goldman et al. |
| 7,008,413 B2 | 3/2006 | Kovach et al. |
| 7,047,082 B1 | 5/2006 | Schrom et al. |
| 7,047,084 B2 | 5/2006 | Erickson et al. |
| 7,054,692 B1 | 5/2006 | Whitehurst et al. |
| 7,058,446 B2 | 6/2006 | Schuler et al. |
| 7,082,333 B1 | 7/2006 | Bauhahn et al. |
| 7,127,297 B2 | 10/2006 | Law et al. |
| 7,142,923 B2 | 11/2006 | North et al. |
| 7,191,014 B2 | 3/2007 | Kobayashi et al. |
| 7,211,050 B1 | 5/2007 | Caplygin |
| 7,216,000 B2 | 5/2007 | Sieracki et al. |
| 7,228,179 B2 | 6/2007 | Campen et al. |
| 7,236,830 B2 | 6/2007 | Gliner |
| 7,239,916 B2 | 7/2007 | Thompson et al. |
| 7,244,150 B1 | 7/2007 | Brase et al. |
| 7,254,445 B2 | 8/2007 | Law et al. |
| 7,294,107 B2 | 11/2007 | Simon et al. |
| 7,299,096 B2 | 11/2007 | Balzer et al. |
| 7,308,302 B1 | 12/2007 | Schuler et al. |
| 7,437,193 B2 | 10/2008 | Parramon et al. |
| 7,565,199 B2 | 7/2009 | Sheffield et al. |
| 7,650,184 B2 | 1/2010 | Walter |
| 7,672,734 B2 | 3/2010 | Anderson et al. |
| 7,680,526 B2 | 3/2010 | McIntyre et al. |
| 7,734,340 B2 | 6/2010 | De Ridder |
| 7,761,165 B1 | 7/2010 | He et al. |
| 7,860,548 B2 | 12/2010 | McIntyre et al. |
| 7,904,134 B2 | 3/2011 | McIntyre et al. |
| 7,945,105 B1 | 5/2011 | Jaenisch |
| 7,949,395 B2 | 5/2011 | Kuzma |
| 7,974,706 B2 | 7/2011 | Moffitt et al. |
| 8,019,439 B2 | 9/2011 | Kuzma et al. |
| 8,175,710 B2 | 5/2012 | He |
| 8,180,601 B2 | 5/2012 | Butson et al. |
| 8,195,300 B2 | 6/2012 | Gliner et al. |
| 8,224,450 B2 | 7/2012 | Brase |
| 8,257,684 B2 | 9/2012 | Covalin et al. |
| 8,262,714 B2 | 9/2012 | Hulvershorn et al. |
| 8,364,278 B2 | 1/2013 | Pianca et al. |
| 8,429,174 B2 | 4/2013 | Ramani et al. |
| 8,452,415 B2 | 5/2013 | Goetz et al. |
| 8,543,189 B2 | 9/2013 | Paitel et al. |
| 8,606,360 B2 | 12/2013 | Butson et al. |
| 8,620,452 B2 | 12/2013 | King et al. |
| 8,918,184 B1 | 12/2014 | Torgerson et al. |
| 2001/0031071 A1 | 10/2001 | Nichols et al. |
| 2002/0032375 A1 | 3/2002 | Bauch et al. |
| 2002/0062143 A1 | 5/2002 | Baudino et al. |

(56) References Cited

U.S. PATENT DOCUMENTS

| | | |
|---|---|---|
| 2002/0087201 A1 | 7/2002 | Firlik et al. |
| 2002/0099295 A1 | 7/2002 | Gil et al. |
| 2002/0115603 A1 | 8/2002 | Whitehouse |
| 2002/0116030 A1 | 8/2002 | Rezei |
| 2002/0123780 A1 | 9/2002 | Grill et al. |
| 2002/0128694 A1 | 9/2002 | Holsheimer |
| 2002/0151939 A1 | 10/2002 | Rezai |
| 2002/0183607 A1 | 12/2002 | Bauch et al. |
| 2002/0183740 A1 | 12/2002 | Edwards et al. |
| 2002/0183817 A1 | 12/2002 | Van Venrooij et al. |
| 2003/0097159 A1 | 5/2003 | Schiff et al. |
| 2003/0149450 A1 | 8/2003 | Mayberg |
| 2003/0171791 A1 | 9/2003 | KenKnight et al. |
| 2003/0212439 A1 | 11/2003 | Schuler et al. |
| 2004/0044378 A1 | 3/2004 | Holsheimer |
| 2004/0044379 A1 | 3/2004 | Holsheimer |
| 2004/0054297 A1 | 3/2004 | Wingeier et al. |
| 2004/0059395 A1 | 3/2004 | North et al. |
| 2004/0133248 A1 | 7/2004 | Frei et al. |
| 2004/0152957 A1 | 8/2004 | Stivoric et al. |
| 2004/0181262 A1 | 9/2004 | Bauhahn |
| 2004/0186532 A1 | 9/2004 | Tadlock |
| 2005/0021090 A1 | 1/2005 | Schuler et al. |
| 2005/0033380 A1 | 2/2005 | Tanner et al. |
| 2005/0049649 A1 | 3/2005 | Luders et al. |
| 2005/0060009 A1 | 3/2005 | Goetz |
| 2005/0070781 A1 | 3/2005 | Dawant et al. |
| 2005/0075689 A1 | 4/2005 | Toy et al. |
| 2005/0085714 A1 | 4/2005 | Foley et al. |
| 2005/0165294 A1 | 7/2005 | Weiss |
| 2005/0228250 A1 | 10/2005 | Bitter et al. |
| 2005/0251061 A1 | 11/2005 | Schuler et al. |
| 2005/0261061 A1 | 11/2005 | Nguyen et al. |
| 2005/0261601 A1 | 11/2005 | Schuler et al. |
| 2005/0261747 A1 | 11/2005 | Schuler et al. |
| 2005/0267347 A1 | 12/2005 | Oster |
| 2005/0288732 A1 | 12/2005 | Schuler et al. |
| 2006/0004422 A1 | 1/2006 | De Ridder |
| 2006/0069415 A1 | 3/2006 | Cameron et al. |
| 2006/0095088 A1 | 5/2006 | De Riddler |
| 2006/0155340 A1 | 7/2006 | Schuler et al. |
| 2006/0206169 A1 | 9/2006 | Schuler |
| 2006/0218007 A1 | 9/2006 | Bjorner et al. |
| 2006/0224189 A1 | 10/2006 | Schuler et al. |
| 2006/0235472 A1 | 10/2006 | Goetz et al. |
| 2006/0259099 A1 | 11/2006 | Goetz et al. |
| 2007/0000372 A1 | 1/2007 | Rezai et al. |
| 2007/0027514 A1 | 2/2007 | Gerber |
| 2007/0067003 A1 | 3/2007 | Sanchez et al. |
| 2007/0078498 A1 | 4/2007 | Rezai et al. |
| 2007/0135855 A1 | 6/2007 | Foshee et al. |
| 2007/0150036 A1 | 6/2007 | Anderson |
| 2007/0162235 A1 | 7/2007 | Zhan et al. |
| 2007/0168004 A1 | 7/2007 | Walter |
| 2007/0168007 A1 | 7/2007 | Kuzma et al. |
| 2007/0191887 A1 | 8/2007 | Schuler et al. |
| 2007/0197891 A1 | 8/2007 | Shachar et al. |
| 2007/0203532 A1 | 8/2007 | Tass et al. |
| 2007/0203537 A1 | 8/2007 | Goetz et al. |
| 2007/0203546 A1* | 8/2007 | Stone .................. A61N 1/0529 607/59 |
| 2007/0265664 A1 | 11/2007 | Gerber et al. |
| 2008/0039895 A1 | 2/2008 | Fowler et al. |
| 2008/0086451 A1 | 4/2008 | Torres et al. |
| 2008/0114233 A1 | 5/2008 | McIntyre et al. |
| 2008/0114579 A1 | 5/2008 | McIntyre et al. |
| 2008/0123923 A1 | 5/2008 | Gielen et al. |
| 2008/0133141 A1 | 6/2008 | Frost |
| 2008/0154341 A1 | 6/2008 | McIntyre et al. |
| 2008/0188734 A1 | 8/2008 | Suryanarayanan et al. |
| 2008/0215118 A1 | 9/2008 | Goetz et al. |
| 2008/0227139 A1 | 9/2008 | Deisseroth et al. |
| 2008/0242950 A1 | 10/2008 | Jung et al. |
| 2008/0261165 A1 | 10/2008 | Steingart et al. |
| 2008/0300797 A1 | 12/2008 | Tabibiazar et al. |
| 2009/0016491 A1 | 1/2009 | Li |
| 2009/0054950 A1 | 2/2009 | Stephens |
| 2009/0118635 A1 | 5/2009 | Lujan et al. |
| 2009/0118786 A1 | 5/2009 | Meadows et al. |
| 2009/0198306 A1 | 8/2009 | Goetz et al. |
| 2009/0198354 A1 | 8/2009 | Wilson |
| 2009/0208073 A1 | 8/2009 | McIntyre et al. |
| 2009/0210208 A1 | 8/2009 | McIntyre et al. |
| 2009/0242399 A1 | 10/2009 | Kamath et al. |
| 2010/0010566 A1 | 1/2010 | Thacker et al. |
| 2010/0023103 A1 | 1/2010 | Elborno |
| 2010/0030312 A1 | 2/2010 | Shen |
| 2010/0064249 A1 | 3/2010 | Groetken |
| 2010/0113959 A1 | 5/2010 | Pascual-Leon et al. |
| 2010/0121409 A1 | 5/2010 | Kothandaraman et al. |
| 2010/0135553 A1 | 6/2010 | Joglekar |
| 2010/0137944 A1 | 6/2010 | Zhu |
| 2010/0152604 A1 | 6/2010 | Kuala et al. |
| 2010/0179562 A1 | 7/2010 | Linker et al. |
| 2010/0324410 A1 | 12/2010 | Paek et al. |
| 2010/0331883 A1 | 12/2010 | Schmitz et al. |
| 2011/0040351 A1 | 2/2011 | Buston et al. |
| 2011/0066407 A1 | 3/2011 | Butson et al. |
| 2011/0172737 A1 | 7/2011 | Davis et al. |
| 2011/0184487 A1 | 7/2011 | Alberts et al. |
| 2011/0196253 A1 | 8/2011 | McIntyre et al. |
| 2011/0213440 A1 | 9/2011 | Fowler et al. |
| 2011/0306845 A1 | 12/2011 | Osorio |
| 2011/0306846 A1 | 12/2011 | Osorio |
| 2011/0307032 A1 | 12/2011 | Goetz et al. |
| 2012/0046715 A1 | 2/2012 | Moffitt et al. |
| 2012/0078106 A1 | 3/2012 | Dentinger et al. |
| 2012/0089205 A1 | 4/2012 | Boyden et al. |
| 2012/0116476 A1 | 5/2012 | Kothandaraman |
| 2012/0165898 A1 | 6/2012 | Moffitt |
| 2012/0165901 A1 | 6/2012 | Zhu et al. |
| 2012/0207378 A1 | 8/2012 | Gupta et al. |
| 2012/0226138 A1 | 9/2012 | DeSalles et al. |
| 2012/0229468 A1 | 9/2012 | Lee et al. |
| 2012/0265262 A1 | 10/2012 | Osorio |
| 2012/0265268 A1 | 10/2012 | Blum et al. |
| 2012/0302912 A1 | 11/2012 | Moffitt et al. |
| 2012/0303087 A1 | 11/2012 | Moffitt et al. |
| 2012/0314924 A1 | 12/2012 | Carlton et al. |
| 2012/0316619 A1 | 12/2012 | Goetz et al. |
| 2013/0039550 A1 | 2/2013 | Blum et al. |
| 2013/0060305 A1 | 3/2013 | Bokil |
| 2013/0116748 A1 | 5/2013 | Bokil et al. |
| 2013/0116749 A1 | 5/2013 | Carlton et al. |
| 2013/0116929 A1 | 5/2013 | Carlton et al. |
| 2014/0067018 A1 | 3/2014 | Carcieri et al. |
| 2014/0277284 A1 | 9/2014 | Chen et al. |
| 2015/0134031 A1 | 5/2015 | Moffitt et al. |

FOREIGN PATENT DOCUMENTS

| | | |
|---|---|---|
| EP | 1559369 | 8/2005 |
| EP | 1372780 | 1/2007 |
| WO | 97/39797 | 10/1997 |
| WO | 98/48880 | 11/1998 |
| WO | 02/26314 | 4/2002 |
| WO | 02/28473 | 4/2002 |
| WO | 02/065896 | 8/2002 |
| WO | 02/072192 | 9/2002 |
| WO | 03/086185 | 10/2003 |
| WO | 2004041080 | 5/2004 |
| WO | 2006017053 | 2/2006 |
| WO | 2006113305 | 10/2006 |
| WO | 2009097224 | 8/2009 |
| WO | 2011025865 | 3/2011 |
| WO | 2012088482 | 6/2012 |

OTHER PUBLICATIONS

Nowinski, W. L., et al., "Statistical analysis of 168 bilateral subthalamic nucleus implantations by means of the probabilistic functional atlas.", Neurosurgery 57(4 Suppl) (Oct. 2005),319-30.

(56) References Cited

OTHER PUBLICATIONS

Obeso, J. A., et al., "Deep-brain stimulation of the subthalamic nucleus or the pars interna of the globus pallidus in Parkinson's disease.", N Engl J Med., 345{13I. The Deep-Brain Stimulation for Parkinson's Disease Study Group, (Sep. 27, 2001 ),956-63.

Fisekovic et al., "New Controller for Functional Electrical Stimulation Systems", Med. Eng. Phys. 2001; 23:391-399.

Patrick, S. K., et al., "Quantification of the UPDRS rigidity scale", IEEE Transactions on Neural Systems and Rehabilitation Engineering, [see also IEEE Trans. on Rehabilitation Engineering 9(1). (2001),31-41.

Phillips, M. D., et al., "Parkinson disease: pattern of functional MR imaging activation during deep brain stimulation of subthalamic nucleus—initial experience", Radiology 239(1). (Apr. 2006),209-16.

Merrill, D. R., et al., "Electrical stimulation of excitable tissue: design of efficacious and safe protocols", J Neurosci Methods. 141(2), (Feb. 15, 2005), 171-98.

Montgomery, E. B., et al., "Mechanisms of deep brain stimulation and future technical developments.", Neurol Res. 22(3). (Apr. 2000),259-66.

Moss, J. , et al., "Electron microscopy of tissue adherent to explanted electrodes in dystonia and Parkinson's disease", Brain, 127{Pt 12). (Dec. 2004),2755-63.

Hunka, K. et al., Nursing Time to Program and Assess Deep Brain Stimulators in Movement Disorder Patients, J. Neursci Nurs., 37: 204-10 (Aug. 2005).

Miocinovic, S., et al., "Sensitivity of temporal excitation properties to the neuronal element activated by extracellular stimulation", J Neurosci Methods. 132(1). (Jan. 15, 2004), 91-9.

Le Bihan, D., et al., "Diffusion tensor imaging: concepts and applications," J Magn Reson Imaging, 13(4) (Apr. 2001), pp. 534-546.

Krack, P., et al., "Postoperative management of subthalamic nucleus stimulation for Parkinson's disease," Mov. Disord., vol. 17(suppl 3) (2002), pp. 188-197.

Jones, DK., et al., "Optimal strategies for measuring diffusion in anisotropic systems by magnetic resonance imaging," Magn. Reson. Med., 42(3) (Sep. 1999), pp. 515-525.

Jezernik, S., et al., "Neural network classification of nerve activity recorded in a mixed nerve," Neurol Res. 23(5) (Jul. 2001), pp. 429-434.

Holsheimer, J., et al., "Identification of the target neuronal elements in electrical deep brain stimulation," Eur J Neurosci., 12(12) (Dec. 2000), pp. 4573-4577.

Hoekema, R., et al., "Multigrid solution of the potential field in modeling electrical nerve stimulation," Comput Biomed Res., 31(5) (Oct. 1998), pp. 348-362.

Hodaie, M., et al., "Chronic anterior thalamus stimulation for intractable epilepsy," Epilepsia, 43(6) (Jun. 2002), pp. 603-608.

Foster, K. R., et al., "Dielectric properties of tissues and biological materials: a critical review.", Grit Rev Biomed Ena. 17(1 ).{1989),25-104.

McIntyre Cameron , et al., "Finite element analysis of the current-density and electric field generated by metal microelectrodes", Ann Biomed Eng . 29(3), (2001 ),227-235.

Mayr et al., "Basic Design and Construction of the Vienna FES Implants: Existing Solutions and Prospects for New Generations of Implants", Medical Engineering & Physics, 2001; 23:53-60.

Wakana, S., et al., "Reproducibility of quantitative tractography methods applied to cerebral white matter," Neuroimage 36 (3) (2007), pp. 630-644.

Viola, et al., "Importance-driven focus of attention," IEEE Trans Vis Comput Graph 12 (5) (2006), pp. 933-940.

Saxena, et al., "Cerebral glucose metabolism in obsessive-compulsive hoarding," Am J Psychiatry. 161 (6) (2004), pp. 1038-1048.

Yianni, John, et al., "Globus pallidus internus deep brain stimulation for dystonic conditions: a prospective audit," Mov. Disord., vol. 18 (2003), pp. 436-442.

Zonenshayn, M., et al., "Comparison of anatomic and neurophysiological methods for subthalamic nucleus targeting," Neurosurgery, 47(2) (Aug. 2000), pp. 282-294.

Voghell et al., "Programmable Current Source Dedicated to Implantabe Microstimulators" ICM '98 Proceedings of the Tenth International Conference, pp. 67-70.

Grill, W. M., et al., "Deep brain stimulation creates an informational lesion of the stimulated nucleus", Neuroreport. 15I7t (May 19, 2004 ), 1137-40.

Adler, DE., et al., "The tentorial notch: anatomical variation, morphometric analysis, and classification in 100 human autopsy cases," J. Neurosurg., 96(6), (Jun. 2002), pp. 1103-1112.

Jones et al., "An Advanced Demultiplexing System for Physiological Stimulation", IEEE Transactions on Biomedical Engineering, vol. 44 No. 12 Dec. 1997, pp. 1210-1220.

Grill, W. M., "Stability of the input-output properties of chronically implanted multiple contact nerve cuff stimulating electrodes," IEEE Transactions on Rehabilitation Engineering [see also IEEE Trans. on Neural Systems and Rehabilitation] (1998), pp. 364-373.

Grill, W. M., "Stimulus waveforms for selective neural stimulation," IEEE Engineering in Medicine and Biology Magazine, 14(4) (Jul.-Aug. 1995), pp. 375-385.

Grill, W. M., et al., "Temporal stability of nerve cuff electrode recruitment properties," IEEE 17th Annual Conference Engineering in Medicine and Biology Society, vol. 2 (1995), pp. 1089-1090.

Gross, RE., et al., "Advances in neurostimulation for movement disorders," Neurol Res., 22(3) (Apr. 2000), pp. 247-258.

Guridi et al., "The subthalamic nucleus, hemiballismus and Parkinson's disease: reappraisal of a neurological dogma," Brain, vol. 124, 2001, pp. 5-19.

Haberler, C. et al., "No tissue damage by chronic deep brain stimulation in Parkinson's disease," Ann Neurol., 48(3) (Sep. 2000), pp. 372-376.

Hamel, W, et al., "Deep brain stimulation of the subthalamic nucleus in Parkinson's disease: evaluation of active electrode contacts," J Neurol Neurosurg Psychiatry, 74(8) (Aug. 2003), pp. 1036-1046.

Hanekom, "Modelling encapsulation tissue around cochlear implant electrodes," Med. Biol. Eng. Comput. vol. 43 (2005), pp. 47-55.

Haueisen, J , et al., "The influence of brain tissue anisotropy on human EEG and MEG," Neuroimage, 15(1) (Jan. 2002), pp. 159-166.

D'Haese et al. Medical Image Computing and Computer-Assisted Intervention—MICCAI 2005 Lecture Notes in Computer Science, 2005, vol. 3750, 2005, 427-434.

Rohde et al. IEEE Transactions on Medical Imaging, vol. 22 No. 11, 2003 p. 1470-1479.

Dawant et al., Biomedical Image Registration. Lecture Notes in Computer Science, 2003, vol. 2717, 2003, 142-150.

Miocinovic et al., "Stereotactiv Neurosurgical Planning, Recording, and Visualization for Deep Brain Stimulation in Non-Human Primates", Journal of Neuroscience Methods, 162:32-41, Apr. 5, 2007, XP022021469.

Gemmar et al., "Advanced Methods for Target Navigaton Using Microelectrode Recordings in Stereotactic Neurosurgery for Deep Brain Stimulation", 21st IEEE International Symposium on Computer-Based Medical Systems, Jun. 17, 2008, pp. 99-104, XP031284774.

Acar et al., "Safety Anterior Commissure-Posterior Commissure-Based Target Calculation of the Subthalamic Nucleus in Functional Stereotactic Procedures", Stereotactic Funct. Neurosura., 85:287-291, Aug. 2007.

Andrade-Souza, "Comparison of Three Methods of Targeting the Subthalamic Nucleus for Chronic Stimulation in Parkinson's Disease", Neurosurgery, 56:360-368, Apr. 2005.

Anheim et al., "Improvement in Parkinson Disease by Subthalamic Nucleus Stimulation Based on Electrode Placement", Arch Neural., 65:612-616, May 2008.

Butson et al., "Tissue and Electrode Capacitance Reduce Neural Activation Volumes During Deep Brain Stimulation", Clinical Neurophysiology, 116:2490-2500, Oct. 2005.

Butson et al., "Sources and Effects of Electrode Impedance During Deep Brain Stimulation", Clinical Neurophysiology, 117:44 7-454, Dec. 2005.

(56) References Cited

OTHER PUBLICATIONS

D'Haese et al., "Computer-Aided Placement of Deep Brain Stimulators: From Planning to Intraoperative Guidance", IEEE Transaction on Medical Imaging, 24:1469-1478, Nov. 2005.
Gross et al., "Electrophysiological Mapping for the Implantation of Deep Brain Stimulators for Parkinson's Disease and Tremor", Movement Disorders, 21 :S259-S283, Jun. 2006.
Halpern et al., "Brain Shift During Deep Brain Stimulation Surgery for Parkinson's Disease", Stereotact Funct. Neurosurg., 86:37-43, published online Sep. 2007.
Herzog et al., "Most Effective Stimulation Site in Subthalamic Deep Brain Stimulation for Parkinson's Disease", Movement Disorders, 19:1050-1099, published on line Mar. 2004.
Jeon et al., A Feasibility Study of Optical Coherence Tomography for Guiding Deep Brain Probes, Journal of Neuroscience Methods, 154:96-101, Jun. 2006.
Khan et al., "Assessment of Brain Shift Related to Deep Brain Stimulation Surgery", Sterreotact Funct. Neurosurg., 86:44-53, published online Sep. 2007.
Koop et al., "Improvement in a Quantitative Measure of Bradykinesia After Microelectrode Recording in Patients with Parkinson's Disease During Deep Brain Stimulation Surgery", Movement Disorders, 21 :673-678, published on line Jan. 2006.
Lemaire et al., "Brain Mapping in Stereotactic Surgery: A Brief Overview from the Probabilistic Targeting to the Patient-Based Anatomic Mapping", NeuroImage, 37:S109-S115, available online Jun. 2007.
Machado et al., "Deep Brain Stimulation for Parkinson's Disease: Surgical Technique and Perioperative Management", Movement Disorders 21 :S247-S258, Jun. 2006.
Maks et al., "Deep Brain Stimulation Activation Volumes and Their Association with Neurophysiological Mapping and Therapeutic Outcomes", Downloaded from jnnp.bmj.com, pp. 1-21, published online Apr. 2008.
Moran et al., "Real-Time Refinment of Subthalamic Nucleus Targeting Using Bayesian Decision-Making on the Root Mean Square Measure", Movement Disorders, 21: 1425-1431, published online Jun. 2006.
Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.
Winkler et al., The First Evaluation of Brain Shift During Functional Neurosurgery by Deformation Field Analysis, J. Neural. Neurosurg. Psychiatry, 76:1161-1163, Aug. 2005.
Yelnik et al., "A Three-Dimensional, Histological and Deformable Atlas of the Human Basal J Ganglia. I. Atlas Construction Based on Immunohistochemical and MRI Data", NeuroImage, 34:618,-638,Jan. 2007.
Ward, H. E., et al., "Update on deep brain stimulation for neuropsychiatric disorders," Neurobiol Dis 38 (3) (2010), pp. 346-353.
Alberts et al. "Bilateral subthalamic stimulation impairs cognitive-motor performance in Parkinson's disease patients." Brain (2008), 131, 3348-3360, Abstract.
Mayberg, H. S., et al., "Deep brain stimulation for treatment-resistant depression," Neuron, 45(5) (Mar. 3, 2005), pp. 651-660.
An, et al., "Prefronlal cortical projections to longitudinal columns in the midbrain periaqueductal gray in macaque monkeys," J Comp Neural 401 (4)(1998), pp. 455-479.
Mayberg, H. S., et al., "Limbic-cortical dysregulation: a proposed model of depression," J Neuropsychiatry Clin Neurosci. 9 (3) (1997), pp. 471-481.
Carmichael, S. T., et al., "Connectional networks within the orbital and medial prefronlal cortex of macaque monkeys," J Comp Neural 371 (2) (1996), pp. 179-207.
Croxson, et al., "Quantitative investigation of connections of the prefronlal cortex in the human and macaque using probabilistic diffusion tractography," J Neurosci 25 (39) (2005), pp. 8854-8866.

Frankemolle, et al. "Reversing cognitive-motor impairments in Parkinson's disease patients using a computational modelling approach to deep brain stimulation programming," Brain 133 (2010), pp. 746-761.
Freedman, et al., "Subcortical projections of area 25 (subgenual cortex) of the macaque monkey," J Comp Neurol 421 (2) (2000), pp. 172-188.
Giacobbe, et al., "Treatment resistant depression as a failure of brain homeostatic mechanisms: implications for deep brain stimulation," Exp Neural 219 (1) (2009), pp. 44-52.
Goodman, et al., "Deep brain stimulation for intractable obsessive compulsive disorder: pilot study using a blinded, staggered-onset design," Biol Psychiatry 67 (6) (2010), pp. 535-542.
Greenberg, et al., "Deep brain stimulation of the ventral internal capsule/ventral striatum for obsessive-compulsive disorder: worldwide experience," Mol Psychiatry 15 (1) (2010), pp. 64-79.
Greenberg. et al., "Three-year outcomes in deep brain stimulation for highly resistant obsessive-compulsive disorder," Neuropsychopharmacology 31 (11) (2006), pp. 2384-2393.
Gutman, et al., "A tractography analysis of two deep brain stimulation white matter targets for depression," Biol Psychiatry 65 (4) (2009), pp. 276-282.
Haber, et al., "Reward-related cortical inputs define a large striatal region in primates that interface with associative cortical connections, providing a substrate for incentive-based learning," J Neurosci 26 (32) (2006), pp. 8368-8376.
Haber, et al., "Cognitve and limbic circuits that are affected by deep brain stimulation," Front Biosci 14 (2009), pp. 1823-1834.
McIntyre,C. C., et al., "Network perspectives on the mechanisms of deep brain stimulation," Neurobiol Dis 38 (3) (2010), pp. 329-337.
Hua, et al., "Tract probability maps in stereotaxic spaces: analyses of white matter anatomy and tract-specific quantification," Neuroimage 39 (1) (2008), pp. 336-347.
Johansen-Berg, et al., "Anatomical connectivity of the subgenual cingulate region targeted with deep brain stimulation for treatment-resistant depression," Cereb Cortex 18 (6) (2008), pp. 1374-1383.
Kopell, et al., "Deep brain stimulation for psychiatric disorders," J Clin Neurophysiol 21 (1) (2004), pp. 51-67.
Lozano, et al., "Subcallosal cingulate gyrus deep brain stimulation for treatment-resistant depression," Biol Psychiatry 64 (6) (2008), pp. 461-467.
Lujan, et al., "Tracking the mechanisms of deep brain stimulation for neuropsychiatric disorders," Front Biosci 13 (2008), pp. 5892-5904.
Lujan, J.L. et al., "Automated 3-Dimensional Brain Atlas Fitting to Microelectrode Recordings from Deep Brain Stimulation Surgeries," Stereotact. Fune!. Neurosurg. 87(2009), pp. 229-240.
Machado. et al., "Functional topography of the ventral striatum and anterior limb of the internal capsule determined by electrical stimulation of awake patients," Clin Neurophysiol 120 (11) (2009), pp. 1941-1948 . . . .
Malone, et al., "Deep brain stimulation of the ventral capsule/ventral striatum for treatment-resistant depression," Biol Psychiatry 65 (4) (2009), pp. 267-275.
Official Communication for U.S. Appl. No. 12/986,735 mailed on Feb. 12, 2013, 12 pages.
Official Communication for U.S. Appl. No. 12/986,735 mailed on Jul. 19, 2012, 8 pages.
McIntyre, C. C., et al., "How does deep brain stimulation work? Present understanding and future questions.", J Clin Neurophysiol. 21 (1 ). (Jan.-Feb. 2004 ),40-50.
Grill, W. M., "Stimulus waveforms for selective neural stimulation", IEEE Engineering in Medicine and Biology Magazine, 14(4}, (Jul.-Aug. 1995), 375-385.
Plaha, P. , et al., "Stimulation of the caudal zona incerta is superior to stimulation of the subthalamic nucleus in improving contralateral parkinsonism.", Brain 129{Pt 7) (Jul. 2006), 1732-4 7.
Rattay, F, "Analysis of models for external stimulation of axons", IEEE Trans. Biomed. Eng. vol. 33 (1986),974-977.
Rattay, F., "Analysis of the electrical excitation of CNS neurons", IEEE Transactions on Biomedical Engineering 45 (6). (Jun. 1998),766-772.

(56) References Cited

OTHER PUBLICATIONS

Rose, T. L., et al. "Electrical stimulation with Pt electrodes. VIII. Electrochemically safe charge injection limits with 0.2 ms pulses [neuronal application]", IEEE Transactions on Biomedical Engineering, 37(11 }, (Nov. 1990), 1118-1120.

Rubinstein, J. T., et al. "Signal coding in cochlear implants: exploiting stochastic effects of electrical stimulation", Ann Otol Rhinol Laryngol Suppl . . . 191, (Sep. 2003), 14-9.

Schwan, H.P., et al., "The conductivity of living tissues.", Ann NY Acad Sci., 65(6). (AUQ., 1957),1007-13.

Taylor, R. S., et al., "Spinal cord stimulation for chronic back and leg pain and failed back surgery syndrome: a systematic review and analysis of prognostic factors", Spine 30(1 ). (Jan. 1, 2005), 152-60.

Micheli-Tzanakou, E., et al., "Computational Intelligence for target assesment in Parkinson's disease", Proceedings of SPIE vol. 4479. Applications and Science of Neural Networks, Fuzzy Systems, and Evolutionary Computation IV,(2001),54-69.

Volkmann et al., Indroduction to the Programming of Deep Brain Stimulators, Movement Disorders, vol. 17, Suppl. 3, pp. S181-S187(2002).

Geddes, L. A., et al., "The specific resistance of biological material—a compendium of data for the biomedical engineer and physiologist.", Med Biol Ena. 5(3). (May 1967),271-93.

Gimsa, J., et al., "Choosing electrodes for deep brain stimulation experiments—electrochemical considerations.", J Neurosci Methods, 142(2), (Mar. 30, 2005),251-65.

Vidailhet, M. , et al., "Bilateral deep-brain stimulation of the globus pallidus in primary generalized dystonia", N Engl J Med. 352(5) (Feb. 3, 2005),459-67.

Viola, P., et al., "Alignment by maximization of mutual information", International Journal of Com outer Vision 24(2). ( 1997), 137-154.

Volkmann, J. , et al., "Basic algorithms for the programming of deep brain stimulation in Parkinson's disease", Mov Disord., 21 Suppl 14. (Jun. 2006),S284-9.

Walter, B. L., et al., "Surgical treatment for Parkinson's disease", Lancet Neural. 3(12). (Dec. 2004),719-28.

Wei, X. F., et al., "Current density distributions, field distributions and impedance analysis of segmented deep brain stimulation electrodes", J Neural Eng . . . 2(4). (Dec. 2005), 139-47.

Zonenshayn, M. , et al., "Location of the active contact within the subthalamic nucleus (STN) in the treatment of idiopathic Parkinson's disease.", Surg Neurol., 62(3) (Sep. 2004),216-25.

Da Silva et al (A primer on diffusion tensor imaging of anatomical substructures. Neurosurg Focus 15(1): p. 1-4, Article 4, 2003.).

Mcintyre, Cameron C., et al., "Uncovering the mechanisms of deep brain stimulation for Parkinson's disease through functional imaging, neural recording, and neural modeling," Crit Rev Biomed Eng., 30(4-6) (2002), pp. 249-281.

Mcintyre, Cameron C., et al., "Uncovering the mechanism(s) of action of deep brain stimulation: activation, inhibition, or both," Clin Neurophysiol, 115(6) (Jun. 2004), pp. 1239-1248.

Mcintyre, C. C., et al., "Sensitivity analysis of a model of mammalian neural membrane." Biol Cybern., 79(1) (Jul. 1998), pp. 29-37.

Mcintyre, Cameron C., et al., "Selective microstimulation of central nervous system neurons," Annals of biomedical engineering, 28(3) (Mar. 2000), pp. 219-233.

Mcintyre Cameron C., et al., "Modeling the excitability of mammalian nerve fibers: influence of aflerpotentials on the recovery cycle," J Neuophysiol, 87(2) (Feb. 2002), pp. 995-1006.

Mcintyre, C. C., et al., Model-based design of stimulus waveforms for selective microstimulation in the central nervous system,, Proceedings of the First Joint [Engineering in Medicine and Biology, 1999. 21st Annual Conf. and the 1999 Annual FallMeeting of the Biomedical Engineering Soc.] BM ES/EMBS Conference, vol. 1 (1999), p. 384.

Mcintyre, C. C., et al., "Model-based design of stimulus trains for selective microstimulation of targeted neuronal populations," Proceedings of the 23rd Annual International Conference of the IEEE Engineering in Medicine and Biology Society, vol. 1 (2001), pp. 806-809.

Mcintyre, Cameron C., et al., "Model-based Analysis of deep brain stimulation of the thalamus," Proceedings of the Second joint EMBS/BM ES Conference, vol. 3, Annual Fall Meeting of the Biomedical Engineering Society (Cal. No. 02CH37392) IEEEPiscataway, NJ (2002), pp. 2047-2048.

Mcintyre, C. C., et al., "Microstimulation of spinal motoneurons: a model study," Proceedings of the 19th Annual International Conference of the IEEE Engineering in Medicine and Biology society, vol. 5, (1997), pp. 2032-2034.

Mcintyre, C. C., et al., "Extracellular stimulation of central neurons: influence of stimulus waveform and frequency on neuronal output," J. Neurophysiol., 88(4), (Oct. 2002), pp. 1592-1604.

Liu, Haiying, et al., "Intra-operative MR-guided DBS implantation for treating PD and ET," Proceedings of SPIE vol. 4319, Department of Radiology & Neurosurgery, University of Minnesota, Minneapolis, MN 55455 (2001), pp. 272-276.

Levy, AL., et al., "An Internet-connected, patient-specific, deformable brain atlas integrated into a surgical navigation system," J Digit Imaging, 10(3 Suppl 1) (Aug. 1997), pp. 231-237.

Lee, D. C., et al., "Extracellular electrical stimulation of central neurons: quantitative studies," In: Handbook of neuroprosthetic methods, WE Finn and PG Lopresti (eds) CRC Press (2003), pp. 95-125.

Zhang, Y., et al., "Atlas-guided tract reconstruction for automated and comprehensive examination of the white matter anatomy," Neuroimage 52(4) (2010), pp. 1289-1301.

""BioPSE" The Biomedical Problem Solving Environment", htt12://www.sci.utah.edu/cibc/software/index.html, MCRR Center for Integrative Biomedical Computing,(2004).

Andrews, R. J., "Neuroprotection trek—the next generation: neuromodulation I. Techniques—deep brain stimulation, vagus nerve stimulation, and transcranial magnetic stimulation.", Ann NY Acad Sci. 993. (May 2003),1-13.

Carnevale, N.T. et al., "The Neuron Book," Cambridge, UK: Cambridge University Press (2006), 480 pages.

Chaturvedi: "Development of Accurate Computational Models for Patient-Specific Deep Brain Stimulation," Electronic Thesis or Dissertation, Jan. 2012, 162 pages.

Chaturvedi, A. et al.: "Patient-specific models of deep brain stimulation: Influence of field model complexity on neural activation predictions." Brain Stimulation, Elsevier, Amsterdam, NL, vol. 3. No. 2 Apr. 2010, pp. 65-77.

Frankemolle, et al., "Reversing cognitive-motor impairments in Parkinson's disease patients using a computational modeling approach to deep brain stimulation programming," Brian 133 (2010), pp. 746-761.

McIntyre, C.C., et al., "Modeling the excitablitity of mammalian nerve fibers: influence of afterpotentials on the recovery cycle," J Neurophysiol, 87(2) (Feb. 2002), pp. 995-1006.

Peterson, et al., "Predicting myelinated axon activation using spatial characteristics of the extracellular field," Journal of Neural Engineering, 8 (2011), 12 pages.

Warman, et al., "Modeling the Effects of Electric Fields on nerver Fibers; Dermination of Excitation Thresholds," IEEE Transactions on Biomedical Engineering, vol. 39, No. 12 (Dec. 1992), pp. 1244-1254.

Wesselink, et al., "Analysis of Current Density and Related Parameters in Spinal Cord Stimulation," IEEE Transactions on Rehabilitation Engineering, vol. 6, No. 2 Jun. 1998, pp. 200-207.

Andrews, R. J., "Neuroprotection trek—the next generation: neuromodulation II. Applications—epilepsy, nerve regeneration, neurotrophins.", Ann NY Acad Sci. 993 (May 2003), 14-24.

Astrom, M. , et al., "The effect of cystic cavities on deep brain stimulation in the basal ganglia: a simulation-based study", J Neural Eng., 3(2), (Jun. 2006).132-8.

Mouine et al. "Multi-Strategy and Multi-Algorithm Cochlear Prostheses", Biomed. Sci. Instrument, 2000; 36:233-238.

(56) References Cited

OTHER PUBLICATIONS

Back, C., et al., "Postoperative Monitoring of the Electrical Properties of Tissue and Electrodes in Deep Brain Stimulation", Neuromodulation, 6(4), (Oct. 2003 ),248-253.
Baker, K. B., et al., "Evaluation of specific absorption rate as a dosimeter of MRI-related implant heating", J Magn Reson Imaging., 20(2), (Aug. 2004),315-20.
Brown, J. "Motor Cortex Stimulation," Neurosurgical Focus ( Sep. 15, 2001) 11(3):E5.
Budai et al., "Endogenous Opioid Peptides Acting at m-Opioid Receptors in the Dorsal Horn Contribute to Midbrain Modulation of Spinal Nociceptive Neurons," Journal of Neurophysiology (1998) 79(2): 677-687.
Cesselin, F. "Opioid and anti-opioid peptides," Fundamental and Clinical Pharmacology (1995) 9(5): 409-33 (Abstract only).
Rezai et al., "Deep Brain Stimulation for Chronic Pain" Surgical Management of Pain, Chapter 44 pp. 565-576 (2002).
Xu, MD., Shi-Ang, article entitled "Comparison of Half-Band and Full-Band Electrodes for Intracochlear Electrical Stimulation", Annals of Otology, Rhinology & Laryngology (Annals of Head & Neck Medicine & Surgery), vol. 102 (5) pp. 363-367 May 1993.
Bedard, C., et al., "Modeling extracellular field potentials and the frequency-filtering properties of extracellular space", Biophys J .. 86(3). (Mar. 2004),1829-42.
Benabid, A. L., et al., "Future prospects of brain stimulation", Neurol Res:22(3), (Apr. 2000),237-46.
Brummer, S. B., et al., "Electrical Stimulation with Pt Electrodes: II—Estimation of Maximum Surface Redox (Theoretical Non-Gassing) Limits", IEEE Transactions on Biomedical Engineering, vol. BME-24, Issue 5, (Sep. 1977),440-443.
Butson, Christopher R., et al., "Deep Brain Stimulation of the Subthalamic Nucleus: Model-Based Analysis of the Effects of Electrode Capacitance on the Volume of Activation", Proceedings of the 2nd International IEEE EMBS, (Mar. 16-19, 2005),196-197.
Mcintyre, Cameron C., et al., "Cellular effects of deep brain stimulation: model-based analysis of activation and inhibition," J Neurophysiol, 91(4) (Apr. 2004), pp. 1457-1469.
Chaturvedi, A., et al., "Subthalamic Nucleus Deep Brain Stimulation: Accurate Axonal Threshold Prediction with Diffusion Tensor Based Electric Field Models", Engineering in Medicine and Biology Society, 2006. EMBS' 06 28th Annual International Conference of the IEEE, IEEE, Piscataway, NJ USA, Aug. 30, 2006.
Butson, Christopher et al., "Predicting the Effects of Deep Brain Stimulation with Diffusion Tensor Based Electric Field Models" Jan. 1, 2001, Medical Image Computing and Computer-Assisted Intervention-Mic CAI 2006 Lecture Notes in Computer Science; LNCS, Springer, Berlin, DE.
Butson, C. R., et al., "Deep brainstimulation interactive visualization system", Society for Neuroscience vol. 898.7 (2005).
Grill, WM., et al., "Electrical properties of implant encapsulation tissue", Ann Biomed Eng. vol. 22. (1994),23-33.
McNaughtan et al., "Electrochemical Issues in Impedance Tomography", 1st World Congress on Industrial Process Tomography, Buxton, Greater Manchester, Apr. 14-17, 1999.
Hardman, C. D., et al., "Comparison of the basal ganglia in rats, marmosets, macaques, baboons, and humans: volume and neuronal number for the output, internal relay, and striatal modulating nuclei", J Comp Neurol., 445(3). (Apr. 8, 2002),238-55.
Hashimoto, T., et al., "Stimulation of the subthalamic nucleus changes the firing pattern of pallidal neurons", J Neurosci. 23(5). (Mar. 1, 2003),1916-23.
Haslinger, B., et al., "Frequency-correlated decreases of motor cortex activity associated with subthalamic nucleus stimulation in Parkinson's disease.", Neuroimage28(3). (Nov. 15, 2005),598-606.
Haueisen, J, et al., "The influence of brain tissue anisotropy on human EEG and MEG", Neuroimage 15(1) (Jan. 2002),159-166.
Hemm, S., et al., "Deep brain stimulation in movement disorders: stereotactic coregistration of two-dimensional electrical field modeling and magnetic resonance imaging.", J Neurosurg. 103(6): (Dec. 2005),949-55.
Hemm, S., et al., "Evolution of Brain Impedance in Dystonic Patients Treated by GPi Electrical Stimulation", Neuromodulation 7(2) (Apr. 2004),67-75.
Hershey, T., et al., "Cortical and subcortical blood flow effects of subthalamic nucleus stimulation in PD.", Neurology 61(6). (Sep. 23, 2003),816-21.
Herzog, J., et al., "Most effective stimulation site in subthalamic deep brain stimulation for Parkinson's disease", Mov Disord. 19(9). (Sep. 2004),1050-4.
Hines, M. L., et al., "The NEURON simulation environment", Neural Comput. 9(6). (Aug. 15, 1997), 1179-209.
Holsheimer, J., et al. "Chronaxie calculated from current-duration and voltage-duration data", J Neurosci Methods. 97(1). (Apr. 1, 2000),45-50.
Johnson, M. D., et al., "Repeated voltage biasing improves unit recordings by reducing resistive tissue impedances", IEEE Transactions on Neural Systems and Rehabilitation Engineering, [see also IEEE Trans. on Rehabilitation Engineering (2005), 160-165.
Kitagawa, M. et al., "Two-year follow-up of chronic stimulation of the posterior subthalamic white matter for tremor-dominant Parkinson's disease.", Neurosurgery. 56(2). (Feb. 2005),281-9.
Limousin, P., et al., "Electrical stimulation of the subthalamic nucleus in advanced Parkinson's disease", N Engl J Med . . . 339(16), (Oct. 15, 1998), 1105-11.
Mcintyre, Cameron C., et al., "Electric Field and Stimulating Influence generated by Deep Brain Stimulation of the Subthalamaic Nucleus," Clinical Neurophysiology, 115(3) (Mar. 2004), pp. 589-595.
Mcintyre, Cameron C. et al., "Electric field generated by deep brain stimulation of the subthalamic nucleus," Biomedical Engineering Society Annual Meeting, Nashville TN (Oct. 2003), 16 pages.
Mcintyre, Cameron C., et al., "Excitation of central nervous system neurons by nonuniform electric fields," Biophys. J., 76(2) (1999), pp. 878-888.
McNeal, DR., et al., "Analysis of a model for excitation of myelinated nerve," IEEE Trans Biomed Eng., vol. 23 (1976), pp. 329-337.
Micheli-Tzanakou, E., et al., "Computational Intelligence for target assesment in Parkinson's disease," Proceedings of SPIE vol. 4479, Applications and Science of Neural Networks, Fuzzy Systems, and Evolutionary Computation IV (2001 ), pp. 54-69.
Miocinovic, S., et al., "Computational analysis of subthalamic nucleus and lenticular fasciculus activation during therapeutic deep brain stimulation," J Neurophysiol., 96(3) (Sep. 2006), pp. 1569-1580.
Miranda, P. C., et al., "The distribution of currents inducedin the brain by Magnetic Stimulation: a finite element analysis incorporating OT-MRI-derived conductivity data," Proc. Intl. Soc. Mag. Reson. Med. 9 (2001 ), p. 1540.
Miranda, P. C., et al., "The Electric Field Induced in the Brain by Magnetic Stimulation: A 3-D Finite-Element Analysis of the Effect of Tissue Heterogeneity and Anisotropy," IEEE Transactions on Biomedical Enginering, 50(9) (Sep. 2003), pp. 1074-1085.
Moffitt, MA., et al., "Prediction of myelinated nerve fiber stimulation thresholds: limitations of linear models," IEEE Transactions on Biomedical Engineering, 51 (2) (2003), pp. 229-236.
Moro, E, et al., "The impact on Parkinson's disease of electrical parameter settings in STN stimulation," Neurology, 59 (5) (Sep. 10, 2002), pp. 706-713.
Nowak, LG., et al., "Axons, but not cell bodies, are activated by electrical stimulation in cortical gray matter. I. Evidence from chronaxie measurements," Exp. Brain Res., 118(4) (Feb. 1998), pp. 477-488.
Nowak, LG., et al., "Axons, but not cell bodies, are activated by electrical stimulation in cortical gray matter. II. Evidence from selective inactivation of cell bodies and axon initial segments," Exp. Brain Res., 118(4) (Feb. 1998), pp. 489-500.
O'Suilleabhain, PE., et al., "Tremor response to polarity, voltage, pulsewidth and frequency of thalamic stimulation," Neurology, 60(5) (Mar. 11, 2003), pp. 786-790.
Pierpaoli, C., et al., "Toward a quantitative assessment of diffusion anisotropy," Magn Reson Med., 36(6) (Dec. 1996), pp. 893-906.

(56) References Cited

OTHER PUBLICATIONS

Plonsey, R., et al., "Considerations of quasi-stationarity in electrophysiological systems," Bull Math Biophys., 29(4) (Dec. 1967), pp. 657-664.
Ranck, J B., "Specific impedance of rabbit cerebral cortex," Exp. Neurol., vol. 7 (Feb. 1963), pp. 144-152.
Ranck, J B., et al., "The Specific impedance of the dorsal columns of the cat: an anisotropic medium," Exp. Neurol., 11 (Apr. 1965), pp. 451-463.
Ranck, J B., "Which elements are excited in electrical stimulation of mammalian central nervous system: a review," Brain Res., 98(3) (Nov. 21, 1975), pp. 417-440.
Rattay, F., et al., "A model of the electrically excited human cochlear neuron. I. Contribution of neural substructures to the generation and propagation of spikes," Hear Res., 153(1-2) (Mar. 2001), pp. 43-63.
Rattay, F., "A model of the electrically excited human cochlear neuron. II. Influence of the three-dimensional cochlear structure on neural excitability," Hear Res., 153(1-2) (Mar. 2001), pp. 64-79.
Rattay, F., "Arrival at Functional Electrostimulation by modelling of fiber excitation," Proceedings of the Ninth annual Conference of the IEEE Engineering in Medicine and Biology Society (1987), pp. 1459-1460.
Rattay, F., "The influence of intrinsic noise can preserve the temporal fine structure of speech signals in models of electrically stimulated human cochlear neurones," Journal of Physiology, Scientific Meeting of the Physiological Society, London, England, UK Apr. 19-21, 1999 (Jul. 1999), p. 170P.
Rizzone, M., et al., "Deep brain stimulation of the subthalamic nucleus in Parkinson's disease: effects of variation in stimulation parameters," J. Neurol. Neurosurg. Psychiatry., 71(2) (Aug. 2001). pp. 215-219.
Saint-Cyr, J. A., et al., "Localization of clinically effective stimulating electrodes in the human subthalamic nucleus on magnetic resonance imaging," J. Neurosurg., 87(5) (Nov. 2002), pp. 1152-1166.
Sances, A., et al., "In Electroanesthesia: Biomedical and Biophysical Studies," A Sances and SJ Larson, Eds., Academic Press, NY (1975), pp. 114-124.
Sl. Jean, P., et al., "Automated atlas integration and interactive three-dimensional visualization tools for planning and guidance in functional neurosurgery," IEEE Transactions on Medical Imaging, 17(5) (1998), pp. 672-680.
Starr, P.A., et al., "Implantation of deep brain stimulators into the subthalamic nucleus: technical approach and magnetic resonance imaging-verified lead locations," J. Neurosurg., 97(2) (Aug. 2002), pp. 370-387.
Sterio, D., et al., "Neurophysiological refinement of subthalamic nucleus targeting," Neurosurgery, 50(1) (Jan. 2002), pp. 58-69.
Struijk, J. J., et al., "Excitation of dorsal root fibers in spinal cord stimulation: a theoretical study," IEEE Transactions on Biomedical Engineering, 40(7) (Jul. 1993), pp. 632-639.
Struijk, J J., et al., "Recruitment of dorsal column fibers in spinal cord stimulation: influence of collateral branching," IEEE Transactions on Biomedical Engineering, 39(9) (Sep. 1992), pp. 903-912.
Tamma, F., et al., "Anatomo-clinical correlation of intraoperative stimulation-induced side-effects during HF-DBS of the subthalamic nucleus," Neurol Sci., vol. 23 (Suppl 2) (2002), pp. 109-110.
Tarler, M., et al., "Comparison between monopolar and tripolar configurations in chronically implanted nerve cuff electrodes," IEEE 17th Annual Conference Engineering in Medicine and Biology Society, vol. 2 (1995), pp. 1093-1109.
Testerman, Roy L., "Coritical response to callosal stimulation: A model for determining safe and efficient stimulus parameters," Annals of Biomedical Engineering, 6(4) (1978), pp. 438-452.
Tuch, D.S., et al., "Conductivity mapping of biological tissue using diffusion MRI," Ann NY Acad Sci., 888 (Oct. 30, 1999), pp. 314-316.

Tuch, D.S., et al., "Conductivity tensor mapping of the human brain using diffusion tensor MRI," Proc Nall Acad Sci USA, 98(20) (Sep. 25, 2001), pp. 11697-11701.
Veraart, C., et al., "Selective control of muscle activation with a multipolar nerve cuff electrode," IEEE Transactions on Biomedical Engineering, 40(7) (Jul. 1993), pp. 640-653.
Vercueil, L., et al., "Deep brain stimulation in the treatment of severe dystonia," J. Neurol., 248(8) (Aug. 2001 ), pp. 695-700.
Vilalte, "Circuit Design of the Power-on-Reset," Apr. 2000, pp. 1-25.
Vitek, J. L., "Mechanisms of deep brain stimulation: excitation or inhibition," Mov. Disord., vol. 17 (Suppl. 3) (2002), pp. 69-72.
Voges, J., et al., "Bilateral high-frequency stimulation in the subthalamic nucleus for the treatment of Parkinson disease: correlation of therapeutic effect with anatomical electrode position," J. Neurosurg., 96(2) (Feb. 2002), pp. 269-279.
Wakana, S., et al., "Fiber tract-based atlas of human white matter anatomy," Radiology, 230(1) (Jan. 2004), pp. 77-87.
Alexander, DC., et al., "Spatial transformations of diffusion tensor magnetic resonance images," IEEE Transactions on Medical Imaging, 20 (11), (2001), pp. 1131-1139.
Wu, Y. R., et al., "Does Stimulation of the GPi control dyskinesia by activating inhibitory axons?," Mov. Disord., vol. 16 (2001), pp. 208-216.
Yelnik J., et al., "Localization of stimulating electrodes in patients with Parkinson disease by using a three-dimensional atlas-magnetic resonance imaging coregistration method," J Neurosurg., 99(1) (Jul. 2003), pp. 89-99.
Alo, K. M., et al., "New trends in neuromodulation for the management of neuropathic pain," Neurosurgery, 50(4), (Apr. 2002), pp. 690-703, discussion pp. 703-704.
Ashby, P., et al., "Neurophysiological effects of stimulation through electrodes in the human subthalamic nucleus," Brain, 122(PI 10), (Oct. 1999), pp. 1919-1931.
Baker, K. B., et al., "Subthalamic nucleus deep brain stimulus evoked potentials: Physiological and therapeutic implications," Movement Disorders, 17(5), (Sep./Oct. 2002), pp. 969-983.
Bammer, R. et al., "Diffusion tensor imaging using single-shot SENSE-EPI", Magn Reson Med., 48(1 ), (Jul. 2002), pp. 128-136.
Basser, P J., et al., "MR diffusion tensor spectroscopy and imaging," Biophys J., 66(1 ), (Jan. 1994), pp. 259-267.
Basser, P J., et al. "New currents in electrical stimulation of excitable tissues," Annu Rev Biomed Eng., 2, (2000), pp. 377-397.
Benabid, AL., et al., "Chronic electrical stimulation of the ventralis intermedius nucleus of the thalamus as a treatment of movement disorders," J. Neurosurg., 84(2), (Feb. 1996), pp. 203-214.
Benabid, AL., et al., "Combinded (Ihalamotoy and stimulation) stereotatic surgery of the VIM thalamic nucleus for bilateral Parkinson disease," Appl Neurophysiol, vol. 50, (1987), pp. 344-346.
Benabid, A L., et al., "Long-term suppression of tremor by chronic stimulation of the ventral intermediate thalamic nucleus," Lancet, 337 (8738), (Feb. 16, 1991 ), pp. 403-406.
Nuttin, et al., "Electrical stimulation in anterior limbs of internal capsules in patients with obsessive-compulsive disorder," Lancet 354 (9189) (1999), p. 1526.
Christensen, Gary E., et al., "Volumetric transformation of brain anatomy," IEEE Transactions on Medical Imaging, 16 (6), (Dec. 1997), pp. 864-877.
Cooper, S , et al., "Differential effects of thalamic stimulation parameters on tremor and paresthesias in essential tremor," Movement Disorders, 17(Supp. 5), (2002), p. S193.
Coubes, P, et al., "Treatment of DYT1-generalised dystonia by stimulation of the internal globus pallidus," Lancet, 355 (9222), (Jun. 24, 2000), pp. 2220-2221.
.Miocinovic, S., et al., "Experimental and theoretical characterization of the voltage distribution generated by deep brain stimulation," Exp Neurol 216 (i) (2009), pp. 166-176.
Dawant, B. M., et al., "Compuerized atlas-guided positioning of deep brain stimulators: a feasibility study," Biomedical Image registration, Second International Workshop, WBIR 2003, Revised Papers (Lecture notes in Comput. Sci. vol. (2717), Springer-Verlag Berlin, Germany(2003), pp. 142-150.

(56) References Cited

OTHER PUBLICATIONS

Finnis, K. W., et al., "3-D functional atalas of subcortical structures for image guided stereotactic neurosurgery," Neuroimage, vol. 9, No. 6, Iss. 2 (1999), p. S206.

Finnis, K. W., et al., "3D Functional Database of Subcorticol Structures for Surgical Guidance in Image Guided Stereotactic Neurosurgery," Medical Image Computing and Computer-Assisted Intervention—MICCAI'99, Second International Conference.Cambridge, UK, Sep. 19-22, 1999, Proceedings (1999), pp. 758-767.

Finnis, K. W., et al., "A 3-Dimensional Database of Deep Brain Functional Anatomy, and Its Application to Image-Guided Neurosurgery," Proceedings of the Third International Conference on Medical Image Computing and Computer-Assisted Intervention. Lecture Notes in Computer Science; vol. 1935 (2000), pp. 1-8.

Finnis, K. W., et al., "A functional database for guidance of surgical and therapeutic procedures in the deep brain," Proceedings of the 22nd Annual International Conference of the IEEE Engineering in Medicine and Biology Society, vol. 3 (2000), pp. 1787-1789.

Finnis, K. W., et al., "Application of a Population Based Electrophysiological Database to the Planning and Guidance of Deep Brain Stereotactic Neurosurgery," Proceedings of the 5th International Conference on Medical Image Computing and Computer-Assisted Intervention—Part 11, Lecture Notes In Computer Science; vol. 2489 (2002), pp. 69-76.

Finnis, K. W., et al., "Subcortical physiology deformed into a patient-specific brain atlas for image-guided stereotaxy," Proceedings of SPIE—vol. 4681 Medical Imaging 2002: Visualization, Image-Guided Procedures, and Display (May 2002), pp. 184-195.

Finnis, Krik W., et al., "Three-Dimensional Database of Subcortical Electrophysiology for Image-Guided Stereotatic Functional Neurosurgery," IEEE Transactions on Medical Imaging, 22(1) (Jan. 2003), pp. 93-104.

Gabriels, L , et al., "Deep brain stimulation for treatment-refractory obsessive-compulsive disorder: psychopathological and neuropsychological outcome in three cases," Acta Psychiatr Scand., 107(4) (2003), pp. 275-282.

Gabriels, LA., et al., "Long-term electrical capsular stimulation in patients with obsessive-compulsive disorder," Neurosurgery, 52(6) (Jun. 2003), pp. 1263-1276.

Goodall, E. V., et al., "Modeling study of activation and propagation delays during stimulation of peripheral nerve fibers with a tripolar cuff electrode," IEEE Transactions on Rehabilitation Engineering, [see also IEEE Trans. on Neural Systems and Rehabilitation], 3(3) (Sep. 1995), pp. 272-282.

Goodall, E. V., et al., "Position-selective activation of peripheral nerve fibers with a cuff electrode," IEEE Transactions on Biomedical Engineering, 43(8) (Aug. 1996), pp. 851-856.

Goodall, E. V., "Simulation of activation and propagation delay during tripolar neural stimulation," Proceedings of the 15th Annual International Conference of the IEEE Engineering in Medicine and Biology Society (1993), pp. 1203-1204.

Grill, WM., "Modeling the effects of electric fields on nerve fibers: influence of tissue electrical properties," IEEE Transactions on Biomedical Engineering, 46(8) (1999), pp. 918-928.

Grill, W. M., et al., "Neural and connective tissue response to long-term implantation of multiple contact nerve cuff electrodes," J Biomed Mater Res., 50(2) (May 2000), pp. 215-226.

Grill, W. M., "Neural modeling in neuromuscular and rehabilitation research," Proceedings of the 23rd Annual International Conference of the IEEE Engineering in Medicine and Biology Society, vol. 4 (2001 ), pp. 4065-4068.

Grill, W. M., et al., "Non-invasive measurement of the input-output properties of peripheral nerve stimulating electrodes," Journal of Neuroscience Methods, 65(1) (Mar. 1996), pp. 43-50.

Grill, W. M., et al., "Quantification of recruitment properties of multiple contact cuff electrodes," IEEE Transactions on Rehabilitation Engineering, [see also IEEE Trans. on Neural Systems and Rehabilitation], 4(2) (Jun. 1996), pp. 49-62.

Grill, W. M., "Spatially selective activation of peripheral nerve for neuroprosthetic applications," Ph.D. Case Western Reserve University, (1995), pp. 245 pages.

\* cited by examiner

REVERSING COGNITIVE-MOTOR IMPAIRMENTS IN PATIENTS HAVING A NEURO-DEGENERATIVE DISEASE USING A COMPUTATIONAL MODELING APPROACH TO DEEP BRAIN STIMULATION PROGRAMMING

CROSS-REFERENCE TO RELATED APPLICATION

The present application is a continuation of U.S. patent application Ser. No. 12/986,735, filed Jan. 7, 2011, which is a continuation-in-part application of International Patent Application No. PCT/US10/58770, filed Dec. 2, 2010, which claims priority to U.S. Provisional Patent Application No. 61/265,782, filed Dec. 2, 2009, the entire contents of each of which is hereby incorporated by reference herein.

GOVERNMENT RIGHTS

Using the specific language required by 37 C.F.R. §401.14(f)(4): This invention was made with government support under grant numbers R01 NS058706 and R01 NS059736 awarded by the National Institutes of Health. The government has certain rights in the invention.

FIELD OF THE INVENTION

The present invention relates to a system and method for stimulating anatomic regions and/or for selecting parameters for such stimulation.

BACKGROUND

Deep brain stimulation (DBS) in the subthalamic nucleus (STN) and other forms of neuromodulation are effective and safe surgical procedures that have been shown to reduce the motor dysfunction of advanced Parkinson's disease (PD) patients. Bilateral DBS refers to stimulation on both sides of the brain, while unilateral DBS refers to stimulation on one side of the brain. Bilateral and unilateral DBS typically target one of three areas, including the STN, GPI, VIM. Bilateral STN DBS has been associated with declines in cognitive and cognitive-motor functioning. DBS is similarly used to treat other neuro-degenerative diseases including cognitive, motor, and cognitive-motor disorders, but presently used stimulation parameters result in detrimental side effects.

SUMMARY

Activities of daily living are typically performed under modestly complex conditions and have cognitive and motor components that are performed simultaneously (Cahn-Weiner, D. A. et al., "Tests of executive function predict instrumental activities of daily living in community-dwelling older individuals," Appl. Neuropsychol. 9, 187-91 (2002) (hereinafter "Cahn-Weiner et al., 2002"), the entire contents of which is hereby incorporated by reference herein). Frontal and executive dysfunction in the elderly and PD patients without DBS can be predictive of cognitive and motor function during ADLs (Cahn-Weiner et al., 2002; Cahn, D. A. et al., "Differential contributions of cognitive and motor component processes to physical and instrumental activities of daily living in Parkinson's disease," Arch Clin Neuropsychol. 13, 575-83 (1998) (hereinafter "Cahn et al., 1998"), the entire contents of each of which is hereby incorporated by reference herein). Understanding how PD and DBS impact cognitive and motor function under conditions requiring greater cognitive rigor and during the simultaneous performance of cognitive and motor tasks may provide a more accurate assessment of the effect of a set of stimulation parameters on cognitive and motor performance when patients are completing "real world" tasks. Current methods of assessing cognitive and motor function in a clinical environment may not be sufficiently demanding or sensitive enough to reveal changes in cognitive or motor performance that occur when either component of a task is increased. There is an emerging body of literature indicating a paradox between the clinical improvements in motor functioning associated with STN DBS and the patient and caregiver's level of postoperative satisfaction (Agid, Y. et al., "Neurosurgery in Parkinson's disease: the doctor is happy, the patient less so?," J. Neural Transm. Suppl. 409-14 (2006); Schupbach, M. et al., "Neurosurgery in Parkinson disease: a distressed mind in a repaired body?," Neurology 66, 1811-6 (2006) (hereinafter "Schupbach et al., 2006"); Schupbach, M. et al., "Psychosocial adjustment after deep brain stimulation in Parkinson's disease," Nature Clinical Practice 4, 58-59 (2008) (hereinafter "Schupbach and Agid, 2008"), the entire contents of each of which is hereby incorporated by reference herein).

Spread of current to non-motor areas of the STN may cause declines in cognitive and cognitive-motor functioning. A study was performed to assess and compare the cognitive-motor performance in advanced PD patients with bilateral STN DBS parameter settings determined clinically (Clinical), e.g., by subjective assessment such as asking a patient how the patient feels or observation of side effects due to stimulation, and with bilateral STN DBS parameter settings derived from a patient-specific computational model (Model), according to which current creep to non-motor regions was minimized or removed altogether. In this regard, the conventional method of parameter selection did not contemplate consideration of reduction of current creep to non-motor regions, but rather were selected largely on the subjective clinical measures, such that if one or more symptoms improved to some degree and there was no side effect noticed, then the parameters associated with those results were deemed worthy of use, without consideration of effect on creep to the non-motor regions. It was also conventionally not known that the spread of current to non-motor regions would negatively affect motor skill.

In the study, data were collected from 10 advanced PD patients, off medication, under three DBS conditions: OFF, Clinical and Model based stimulation. Clinical stimulation parameters had been determined based on clinical evaluations and the parameters were stable, i.e., unchanged, for at least six months prior to study participation. Model based parameters were selected to minimize the spread of current to non-motor portions of the STN using Cicerone DBS software (See Miocinovic S. et al., "Cicerone: stereotactice neurophysiological recording and deep brain stimulation electrode placement software system," Acta Neurochir Suppl., 97, 561-7 (2007) (hereinafter "Miocinovic et al., 2007"), which is incorporated by reference herein). That is, in the study, and according to an example embodiment of the invention, software is used that provides a 2D or 3D visualization of patient images, DBS electrodes, and/or calculated estimated/predicted volumes of activation for specified stimulation parameters. Based on those visualizations, an operator is able to modify the parameters until a VTA is provided that has minimal current spread to non-motor portions of the brain. In fact such visualization and tinkering until selection of parameters for use may be performed without the presence of the patient.

For each stimulation condition (OFF, Clinical, and Model), participants performed a working memory (n-back task) and motor task (force-tracking) under single- and dual-task settings. During the dual-task, participants performed the n-back and force-tracking tasks simultaneously. Clinical and Model parameters were equally effective in improving the Unified Parkinson's disease Rating Scale (UPDRS-III) scores relative to Off DBS scores, e.g., with respect to motor response as measured by the UPDRS-III. The average improvement in off medication UPDRS-III scores for both parameter settings, 46 percent, is within the range of improvement typically reported in long-term studies with bilateral STN DBS in advanced PD patients (Abelson, J. L. et al., "Deep brain stimulation for refractory obsessive-compulsive disorder," Biol Psychiatry. 57, 510-6 (2005); Kumar, R. et al., "Long-term follow-up of thalamic deep brain stimulation for essential and parkinsonian tremor," Neurology. 61, 1601-4 (2003); Rodriguez-Oroz, M. C. et al., "Bilateral deep brain stimulation in Parkinson's disease: a multicentre study with 4 years follow-up," Brain 128, 2240-9 (2005); Weaver, F. M. et al., "Bilateral deep brain stimulation vs best medical therapy for patients with advanced Parkinson disease: a randomized controlled trial," Jama. 301, 63-73 (2009), the entire contents of each of which is hereby incorporated by reference herein). The inventors discovered that the n-back and force-tracking tasks, administered as described herein to obtain the test results described herein, provide a better context in which activities of daily living are completed, as most ADLS have a cognitive and motor component, and therefore provide a better measure than UPDRS for determining effectiveness of stimulation parameters.

Single-task working memory declines, in the 2-back condition, were significantly less under Model compared to Clinical DBS settings. Under dual-task conditions, force tracking was significantly better with Model compared to Clinical DBS. These results indicate that the cognitive and cognitive-motor declines associated with bilateral STN DBS may be reversed, without compromising motor benefits, by utilizing stimulation parameters that minimize current spread into non-motor regions of the STN. Theoretically, it is conceivable that there may be a task that is 100% motor related, without any cognitive function required, in which case it may occur that there would be no performance difference between Clinical and Model parameters, but almost no ADLs are purely motor.

Indeed, the transmission of pathological information within the basal ganglia thalamocortical circuits is thought to underlie the symptoms of PD (Albin, R. L. et al., "The functional anatomy of basal ganglia disorders," Trends Neurosci 12, 366-375 (1989); DeLong, M. R., "Primate models of movement disorders of basal ganglia origin," Trends. Neurosci. 13, 281-285 (1990); Llinas, R. R. et al., "Thalamocortical dysrhythmia: a neurological and neuropsychiatric syndrome characterized by magnetoencephalography," Proc. Natl. Acad. Sci. U.S.A. 96 (1999); Timmermann, L. et al., "The cerebral oscillatory network of parkinsonian resting tremor," Brain 126, 199-212 (2003); Vitek, J. L. et al., "Physiology of hypokinetic and hyperkinetic movement disorders: model for dyskinesia," Ann. Neurol. 47, S131-S140 (2000), the entire contents of each of which is hereby incoporated by reference herein). It is believed that DBS acts to regularize activity within the motor circuit thereby reducing the passage of pathological information from the pallidum (Grill, W. M. et al., "Deep brain stimulation creates an informational lesion of the stimulated nucleus," Neuroreport 15, 1137-40 (2004); Guo, Y. et al., "Thalamocortical relay fidelity varies across subthalamic nucleus deep brain stimulation protocols in a data-driven computational model," J Neurophysiol. 99, 1477-92 (2008); Hashimoto, T. et al., "Stimulation of the subthalamic nucleus changes the firing pattern of pallidal neurons," J Neurosci. 23, 1916-23 (2003), the entire contents of each of which is hereby incoporated by reference herein). The spread of current to non-motor regions of the STN is likely to disrupt the spread of non-pathological information from these non-motor regions of the STN. Disruption of information processing in these non-motor regions may be responsible for the DBS related cognitive-motor declines observed under dual-task conditions. The loss of transmitted information or information processing capabilities may not produce a deficit in cognitive function following unilateral procedures (Alberts, J. L. et al., "Bilateral subthalamic stimulation impairs cognitive-motor performance in Parkinson's disease patients," Brain 131, 3348-60 (2008) (herein after "Alberts et al., 2008"), the entire contents of which is hereby incorporated by reference) or when the patients are able to focus all of their attention on the performance of a cognitive or motor task alone, as is the case during most clinical examinations. However, as the cognitive demands of the task increase, information processing demands increase. Therefore, under bilateral STN DBS with conventional Clinically determined stimulation parameters, which results in spread of current to non-motor regions, such current spread may compromise cognitive-motor functioning. Cognitive resources on which patients may attempt to draw may now be even more compromised as a result of bilateral disruption of non-motor pathways. The Model parameters according to the present invention, set to avoid spread to non-motor regions may minimize or avoid such further degeneration of cognitive resources.

Further in this regard, the focus of clinical programming has been on the motor response, and unless non-motor side effects are readily apparent, they are generally not detected; particularly those that may only arise under more complex testing conditions. In turn, unintentional over-stimulation can occur when the stimulus amplitude at a therapeutic contact is adjusted to be just below threshold for motor side effects, related to assumption that more stimulation is better than less. However, the study conducted by the inventors indicates that Model parameters resulted in similar improvements in clinical ratings and minimized cognitive-motor declines under dual-task conditions compared to Clinical settings, while using significantly less power (cf Table 4 below). Model parameters were selected to both focus a volume of tissue activated (VTA) on the target region and to be energy efficient. Previous clinical studies have found no significant benefit from using stimulation frequencies greater than 100-130 Hz (Moro, E. et al., "The impact on Parkinson's disease of electrical parameter settings in STN stimulation," Neurology 59, 706-13 (2002) (hereinafter "Moro et al., 2002"; Rizzone, M. et al., "Deep brain stimulation of the subthalamic nucleus in Parkinson's disease: effects of variation in stimulation parameters," J. Neurol. Neurosurg. Psychiatry 71, 215-9 (2001), the entire contents of each of which is hereby incorporated by reference herein), and from the biophysical perspective of axonal activation the most energy efficient pulse width available in the Medtronic Soletra/Kinetra DBS system is 60 µs in a monopolar configuration (Butson and McIntyre, 2007; Sahin, M. et al., "Non-rectangular waveforms for neural stimulation with practical electrodes," J. Neural Eng. 4, 227-33 (2007), the entire contents of each of which is hereby incoporated by reference herein). Therefore, the Model DBS parameters according to the present invention may be selected with these constraints, resulting in reduced power consumption that could help to minimize the threat of stimulation induced tissue damage and prolong battery life expectancy.

In addition to better overall cognitive-motor performance associated with Model parameters, the amount of power consumed was, on average, less than half of the Clinical settings.

Although the present invention is described in relation to Parkinson's Disease and the STN, the methods and systems of the present invention can be used by patients suffering from medical disorders. In preferred embodiments, the medical disorders are characterized by abnormal motor function, such as in patient's limbs (upper and/or lower extremities). The medical disorder can be a neurological disorder (i.e., a disorder of the patient's nervous system). In certain embodiments, the neurological disorder is a neuro-motor or neurocognitive disorder that results in abnormal motor function and that is characterized by irregular motor cortical output including, for example, output from the cerebellum and/or supplementary motor area ("SMA") of the cortex; and irregular sub-cortical output from regions that contribute to motor function in a patient such as, for example, the basal ganglia, the subthalamic nucleus and/or the thalamus.

The methods have application to mammalian patients, including humans suffering from the above-described disorders. In certain embodiments, the neuromotor or neurocognitive disorders are degenerative in nature. Exemplary disorders include PD, Alzheimer's Disorder, dementia, Parkinsonian syndrome, essential tremor, multiple sclerosis (MS), amyotrophic lateral sclerosis (ALS), traumatic brain injury, stroke, multiple system atrophy (MSA), and dystonia.

Embodiments of the present invention are directed to a system and method for stimulating an anatomical region in a stimulation procedure in which less than 10% of non-motor regions (i.e., regions not associated with motor function), e.g., of the brain, are stimulated. In an example embodiment, one or more of the zona incerta, lenticular fasciculus, and motor region of the globus pallidus and internal capsule are stimulated, while less than 10% of non-motor anatomical-neural regions of the globus pallidus or STN are stimulated.

In an example embodiment of the present invention, an anatomical region is stimulated in a stimulation procedure in which at least one of the zona incerta, lenticular fasciculus, and motor region of the globus pallidus and internal capsule are stimulated, while current is not spread to, and therefore there is no stimulation of, any of the corticospinal tract (CS), corticobulbar tract (CB), and the non-motor regions of the globus pallidus (GP) and internal capsule.

For example, a target VTA may be created, for example, according to methods described in U.S. patent application Ser. No. 12/266,394, entitled "3D Atlas Fitting Using Micro-Electrode Recordings" and filed Nov. 6, 2008, in U.S. Provisional Patent Application Ser. No. 61/120,006, entitled "System and Method to Define Target Volume for Stimulation in the Brain" and filed Dec. 4, 2008, in International Patent Application No. PCT/US09/066821 entitled "System and Method to Define Target Volume for Stimulation in the Brain" and filed Dec. 4, 2009, in U.S. patent application Ser. No. 12/869,159, entitled "System and Method to Estimate Region of Tissue Activation" and filed Aug. 26, 2010, and in International Patent Application No. PCT/US1046772, entitled "System and Method to Estimate Region of Tissue Activation" and filed Aug. 26, 2010, the entire contents of each of which is hereby incorporated by reference in its entirety, such that they include no or minimal spread of current to the non-motor regions.

Example embodiments of the present invention are directed to a system and method for selection of stimulation parameters for treatment of neuro-degenerative disorders, such as neuro-cognitive and/or neuro-motor disorders based on results of tests of cognitive function, tests of motor function, and a combination of such tests, performed by the patient to which stimulation is to be performed using the selected stimulation parameters. The stimulation may be performed using implanted electrodes. In an example embodiment, the test results may be used for selection of stimulation parameters that minimize creep of current to non-motor anatomic regions, e.g., of the brain. In an example embodiment, the n-Back test may be used as the test for testing cognitive function, a force-maintenance task may be used as the test for testing motor function, and a test where a patient is subjected to both the n-Back test and the force-maintenance task simultaneously may be used as the combination as a "dual task."

In alternative example embodiments of the present invention, the motor and cognitive testing discussed throughout the present application may be performed using motor, cognitive, and/or motor-cognitive tests described in U.S. Provisional Pat. App. Ser. No. 61/262,662, filed Nov. 19, 2009 ("the '662 application") and/or in International Pat. App. No. PCT/US10/57453, filed Nov. 19, 2010 ("the '453 application"), the entire contents of each of which is hereby incorporated by reference herein. Those tests may be administered and the test results captured and recorded, for example, as described in the '662 application and/or the '453 application.

U.S. Provisional patent Application No. 61/409,693, entitled "Improving Postural Stability with STN DBS" and filed Nov. 3, 2010, the entire contents of which is hereby incorporated by reference in its entirety describes further application and details of the features described herein concerning stimulation parameters selected for minimizing spread of current to and stimulation of non-motor anatomical regions.

Example embodiments of the present invention are directed to a computer system configured to determine stimulation parameters based on the above-described tests, e.g., to minimize creep of current to non-motor anatomical regions. That is, to determine stimulation parameters, the system may evaluate various parameter settings using objective and quantitative test that have cognitive and motor components.

Programming DBS devices for maximal clinical benefit and minimal side effects can be a difficult and time consuming process, requiring a highly trained and experienced individual to achieve desirable results (Hunka, K. et al. "Nursing time to program and assess deep brain stimulators in movement disorder patients," J. Neurosci. Nurs. 37, 204-10 (2005); Moro, E. et al., "Subthalamic nucleus stimulation: improvements in outcome with reprogramming," Arch. Neurol. 63, 1266-72 (2006) (hereinafter "Moro et al., 2006"), the entire contents of each of which is hereby incoporated by reference herein). While guidelines exist on stimulation parameter settings that are typically effective (Moro et al., 2002; Rizzone et al., 2001; Volkmann, J. et al., "Basic algorithms for the programming of deep brain stimulation in Parkinson's disease," Mov. Disord. 21 Suppl. 14, S284-9 (2006), the entire contents of each of which is hereby incorporated by reference herein), these vary from patient to patient and it is not practical to clinically evaluate each of the thousands of stimulation parameter combinations that are possible in order to optimize DBS in each patient. As a result, the therapeutic benefits achieved with DBS are strongly dependent on the intuitive skill and experience of the clinician performing the programming (Moro et al., 2006) and the amount of time each programmer can allocate to that patient.

Rather than relying solely on intuition and experience, clinical DBS programming according to the present invention can be augmented with visualization of electrode location and theoretical calculation of an optimal VTA. Software technology can provide an initial starting point for the clinical programming process, thereby focusing patient testing on a select range of stimulation settings where an abbreviated version of the dual-task paradigm could be performed to evaluate cognitive and motor function. For example, the VTA may be visualized before the programming user even sees the patient. The programming user can essentially test a host of parameter sets using the software rather than having to actually apply those parameters to stimulation of the patient. The parameters that are most likely ineffective may therefore be eliminated to begin with. Additionally, the software itself may be programmed with parameter sets that are most likely ineffective due to, for example, current creep to non-motor regions, and may accordingly output suggested sets of parameter settings. The dual-task paradigm could concentrate clinical resources on maximizing clinical outcomes and minimize time consuming searches through the DBS parameter space (contact, voltage, pulse width, frequency).

According to an example embodiment of the present invention, cognitive and motor performance may be evaluated simultaneously, e.g., by administering the above-described tests, during DBS programming while visualizing VTAs associated with specific DBS parameters. This may mitigate the described paradoxical situation between the clinical improvements in motor functioning and the patient and caregiver's level of postoperative satisfaction. That is, by modifying DBS parameters based on the test results, the patient satisfaction to the DBS programming using the resultant stimulation parameters may be consistent with the motor benefits.

In this regard, by visualizing the various VTAs while simultaneously assessing the cognitive and motor performance as described herein, the medical clinician may be able to rank various VTAs according to such performance and modify the target VTAs until stimulation parameters are provided for a closely matching estimated VTA that produces the best cognitive and motor performance. The clinician may input notes in association with VTAs, which notes identify and/or rank the assessed cognitive and motor performance. The system may include a graphical user interface (GUI) that displays an anatomical model, e.g., of the patient brain and implanted leadwire, that further displays with respect to the displayed model one or more areas corresponding to explored VTAs, and that further displays note icons representing the input notes associated with such VTAs and displayed such that it is indicated with which VTAs the corresponding notes are associated. Responsive to selection of the note icons, the system and method may display the notes.

According to an example embodiment of the present invention, the clinician may input a score associated with the explored VTAs based on the cognitive and motor function, and for those VTAs for which a score not meeting a predetermined threshold, the system may treat the VTA as one associated with a side effect. The system and method may visually indicate which explored VTAs are associated with side effects and which are not. Such graphics may be further considered by the clinician to ultimately make a final selection of the stimulation parameters to use.

It is noted that other factors may be used in selection of stimulation parameters, and, while the assessed cognitive and motor performance may be considered, the parameters resulting in the very best performance are not necessarily selected. Accordingly, parameters which result in a good performance, but not necessarily the best, may be selected.

In an example, a system user may select initial parameter settings by inputting a target VTA with minimal current creep to the non-motor regions and obtaining settings that provide an estimated VTA closely matching the target VTA. If the patient performs poorly on the administered tests, a new target VTA may be drawn with even less creep to the non-motor regions or at further distance from such regions, etc. As noted above, the cognitive and motor performance may be tested while visualizing the VTAs associated with particular parameters. The clinician can keep tweaking the target VTAs according to the test performance. That is, the clinician will be able to quickly see the results of the performance and those results relate to the position and size of the VTA.

Example embodiment of the present invention are directed to a computer system configured to provide a GUI via which the computer system may obtain user input according to which the computer system is configured to output a representation of a target VTA. The user input may be stimulation parameters and/or references to anatomical points, e.g., of a perimeter of the target VTA. The computer system may be configured to further provide a GUI via which the user may adjust parameters or points of the target VTA to obtain a desired target VTA. For example, the target VTA may be one that avoids non-motor anatomical regions to the extent described above. In an example embodiment of the present invention, the system may determine stimulation parameter settings that are estimated to provide a VTA that most closely matches the input target VTA. In an example embodiment, the system may operate under a condition that it limits the most closely matching estimated VTA to one that does not protrude beyond any point of the outer perimeter of the target VTA (even though there may be such a VTA that is a closer match to the target VTA).

For obtaining input for the generation of, and for generating, the target VTAs and/or for determining estimated VTAs, and/or for recording and visually outputting notes or indications of notes concerning cognitive and motor performance associated with VTAs, the system and method of the present invention may, for example, use processes described in U.S. patent application Ser. No. 12/454,330, filed May 15, 2009 and entitled "Clinician Programmer System and Method for Calculating Volumes of Activation" ("the '330 application"), in U.S. patent application Ser. No. 12/454,312, filed May 15, 2009 and entitled "Clinician Programmer System and Method for Calculating Volumes of Activation for Monopolar and Bipolar Electrode Configurations" ("the '312 application"), in U.S. patent application Ser. No. 12/454,340, filed May 15, 2009 and entitled "Clinician Programmer System and Method for Steering Volumes of Activation" ("the '340 application"), in U.S. patent application Ser. No. 12/454,343, filed May 15, 2009 and entitled "Clinician Programmer System Interface for Monitoring Patient Progress" ("the '343 application"), and in U.S. patent application Ser. No. 12/454,314, filed May 15, 2009 and entitled "Clinician Programmer System and Method for Generating Interface Models and Displays of Volumes of Activation" ("the '314 application"), the content of each of which is hereby incorporated herein by reference in its entirety.

Example embodiments of the present invention are directed to a computer system configured to monitor a patient performance during, and/or to record results of, the tests described above, the results of which may be used to select the stimulation parameters.

The computer system(s) may include one or more processors, which may be implemented using any conventional processing circuit and device or combination thereof, e.g., a Central Processing Unit (CPU) of a Personal Computer (PC) or other workstation processor, to execute code provided, e.g., on a hardware computer-readable medium including any conventional memory device, to perform any of the methods described herein, alone or in combination. The one or more processors may be embodied in a server or user terminal or combination thereof. The user terminal may be embodied, for example, a desktop, laptop, hand-held device, Personal Digital Assistant (PDA), television set-top Internet appliance, mobile telephone, smart phone, etc., or as a combination of one or more thereof. The memory device may include any conventional permanent and/or temporary memory circuits or combination thereof, a non-exhaustive list of which includes Random Access Memory (RAM), Read Only Memory (ROM), Compact Disks (CD), Digital Versatile Disk (DVD), and magnetic tape.

Example embodiments of the present invention are directed to one or more hardware computer-readable media, e.g., as described above, having stored thereon instructions executable by a processor to perform the methods described herein.

Example embodiments of the present invention are directed to a method, e.g., of a hardware component or machine, of transmitting instructions executable by a processor to perform the methods described herein.

DETAILED DESCRIPTION

Figure 1:
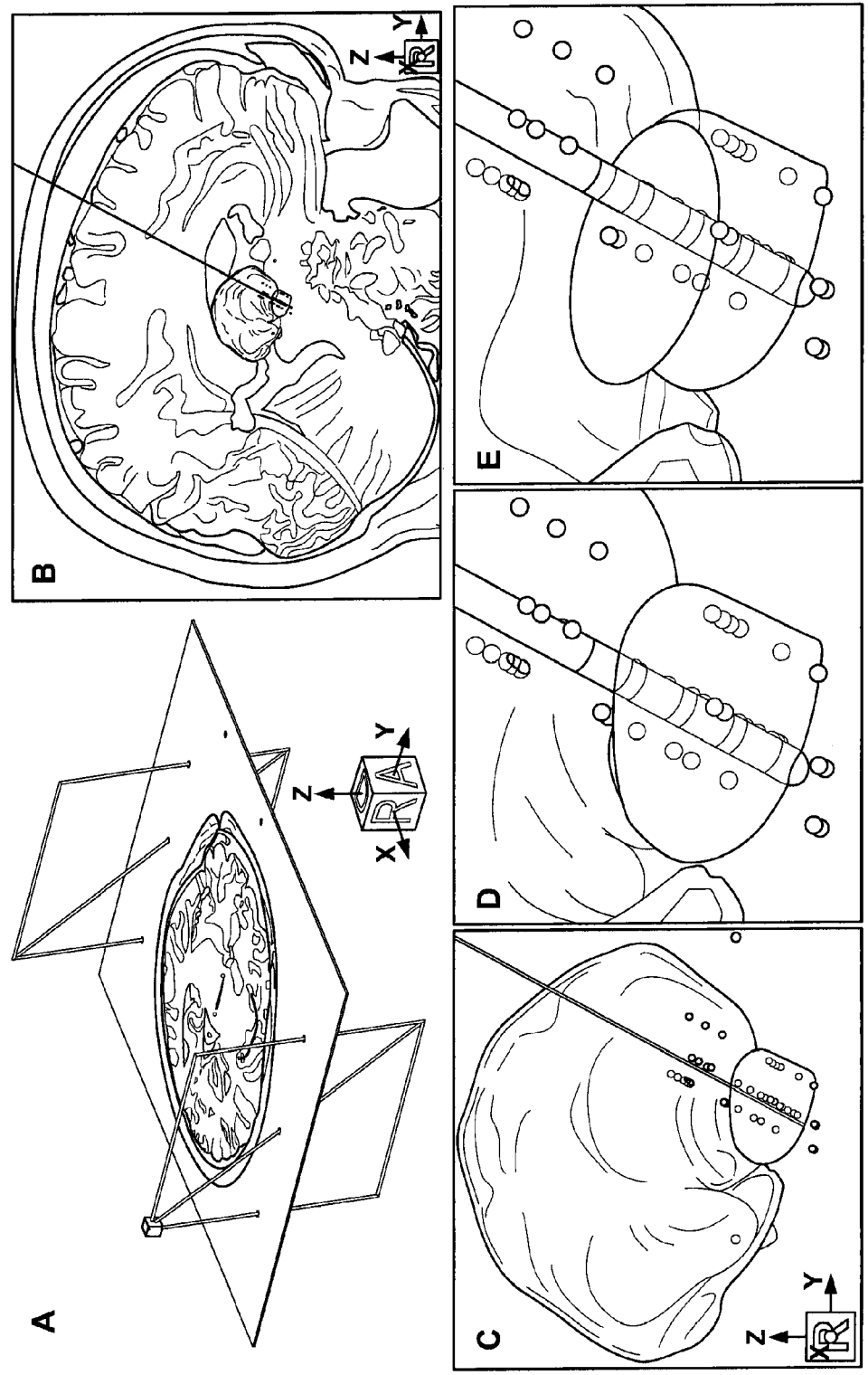
FIG. 1 shows a patient specific model of deep brain stimulation (DBS), where a stereotactic coordinate system was defined relative to the imaging data, microelectrode recording data were entered into the model (thalamic cells, yellow dots; subthalamic cells, green dots; substantia nigra cells, red dots), a three dimensional brain atlas was fitted to the neuroanatomy and neurophysiology (yellow volume, thalamus; green volume, subthalamic nucleus), and a DBS electrode was positioned in the model, pertaining to a theoretical ellipsoid target volume, and referring to data presented for patient No 1.

Bilateral deep brain stimulation (DBS) of the subthalamic nucleus (STN) is an effective therapy for improving the cardinal motor signs of advanced Parkinson's disease (PD) (The Deep Brain Stimulation Study Group, "Deep-brain stimulation of the subthalamic nucleus or the pars interna of the globus pallidus in Parkinson's disease," N. Engl. J. Med. 345, 956-63 (2001), the entire contents of which is hereby incorporated by reference herein). Other target sites are effective for treating other motor, cognitive, and/or cognitive-motor disorders as outlined above. While bilateral STN DBS is considered safe, an emerging concern is the potential negative consequences it may have on cognitive functioning and overall quality of life (Freund, H. J., "Long-term effects of deep brain stimulation in Parkinson's disease," Brain 128, 2222-3 (2005); Rodriguez-Oroz et al., 2005; Saint-Cyr, J. A. et al., "Neuropsychological consequences of chronic bilateral stimulation of the subthalamic nucleus in Parkinson's disease," Brain 123 (Pt 10), 2091-2108 (2000), the entire contents of each of which is hereby incorporated by reference herein). A recent report indicates patients' perceptions of their day-to-day function is improved subtly by DBS; however, caregivers perceived the patient as exhibiting subtle declines in day-to-day functioning (Duff-Canning, S. J. et al., "He said, she said: Differences between self and caregiver ratings of postoperative behavioral changes in Parkinson's disease patients undergoing bilateral subthalamic nucleus deep brain stimulation," In: Twelfth International Congress of Parkinson's disease and Movement Disorders, vol. 23, ed.ˆeds. Wiley-Blackwell, Chicago, Ill., p. S127 (2008), the entire contents of which is hereby incorporated by reference herein).

Several long-term studies examining changes in cognitive function suggest that bilateral STN DBS results in varying levels of decline in overall cognitive functioning, including verbal fluency (Contarino, M. F. et al., "Cognitive outcome 5 years after bilateral chronic stimulation of subthalamic nucleus in patients with Parkinson's disease," J Neurol Neurosurg Psychiatry 78, 248-52 (2007); Funkiewiez, A. et al., "Long term effects of bilateral subthalamic nucleus stimulation on cognitive function, mood, and behaviour in Parkinson's disease," J Neurol Neurosurg Psychiatry 75, 834-9 (2004), the contents of each of which is hereby incorporated by reference herein) and working memory (Rodriguez-Oroz et al., 2005; Schupbach, W. M. et al., "Stimulation of the subthalamic nucleus in Parkinson's disease: a 5 year follow up," J. Neurol. Neurosurg. Psychiatry 76, 1640-4 (2005) (hereinafter "Schupbach et al., 2005"), the entire contents of each of which is hereby incorporated by reference herein). Although some of these long term results may be due to natural progression of PD, they provide compelling evidence to suggest that bilateral STN DBS may adversely affect different features of cognitive functioning and bring into question earlier views that STN DBS does not impair cognition. For example, measures of verbal fluency and learning and memory, exhibited significant declines when comparing bilateral STN DBS to pre-surgery or OFF DBS scores (OFF typically referring to the temporary turn off of DBS for a research or clinical protocol) (Woods, S. P. et al., "Neuropsychological sequelae of subthalamic nucleus deep brain stimulation in Parkinson's disease: a critical review," Neuropsychol. Rev. 12, 111-26 (2002), the entire contents of which is hereby incorporated by reference herein). In a meta-analysis that included data from 1,398 patients with bilateral STN DBS, cognitive problems were seen in 41 percent of patients (Temel, Y. et al., "Behavioural changes after bilateral subthalamic stimulation in advanced Parkinson disease: A systematic review," Parkinsonism Relat. Disord. (2006), the entire contents of which is hereby incoporated by reference herein). Cognitive problems varied from a moderate deterioration in verbal memory to significant declines in executive functioning.

While cognitive declines are commonly seen with STN DBS, the degree of measured effect may be attributable to variation in the difficulty of the cognitive testing across studies Hershey, T. et al., "Stimulation of STN impairs aspects of cognitive control in PD," Neurology 62, 1110-4 (2004), the entire contents of which is hereby incoporated by reference herein). The majority of studies examining the cognitive effects of STN DBS have utilized relatively simple neuropsychological tests suitable for use in a clinical environment. Therefore, reports of no or minimal effect of STN DBS on cognitive functioning may be explained by a lack of difficulty in test selection or the artificial environmental, free of distraction, in which they are completed. Hershey and colleagues (Hershey et al., 2004) reported that bilateral STN stimulation decreased working memory under cognitively demanding conditions. Those results are added to by examining cognitive and motor function individually and simultaneously under different levels of cognitive demands (Alberts et al., 2008). As working memory demands increased, cognitive, motor and cognitive-motor function decreased during bilateral compared to unilateral STN DBS (Alberts et al., 2008). Based on the inventors' results, it is believed that the spread of current to non-motor regions of each STN may be responsible for the disruption in cognitive, motor and cognitive-motor function during bilateral STN DBS.

Given its small size, stimulation within the STN, even with electrode contacts located predominately within the sensorimotor territory, can result in the spread of current to limbic and associative areas as well as to surrounding structures and fiber systems that may also affect cognition (Maks, C. B. et al., "Deep brain stimulation activation volumes and their association with neurophysiological mapping and therapeutic outcomes," J. Neurol. Neurosurg. Psychiatry 80, 659-66 (2009), the entire contents of which is hereby incorporated by reference herein). The electric field generated by DBS is non-discriminately applied to all of the neural elements surrounding the electrode, and these stimulation effects are subsequently transmitted throughout the basal ganglia and thalamocortical networks (Asanuma, K. et al., "Network modulation in the treatment of Parkinson's disease," Brain 129, 2667-78 (2006); Karimi, M. et al., "Subthalamic nucleus stimulation-induced regional blood flow responses correlate with improvement of motor signs in Parkinson disease," Brain 131, 2710-9 (2008); Phillips, M. D. et al., "Parkinson disease: pattern of functional MR imaging activation during deep brain stimulation of subthalamic nucleus—initial experience," Radiology 239, 209-16 (2006), the entire contents of each of which is hereby incorporated by reference herein). In turn, diminished cognitive function may be due to nonselective activation of non-motor pathways within and around the STN. However, according to the present invention, when the STN is stimulated, current spread to limbic and associative regions as well as throughout the basal ganglia and Thalamocortical networks is avoided through software modeling and calculations of those VTAs.

The interplay between the patient and clinician performing the DBS parameter selection is critical in defining the balance between therapeutic benefit and stimulation induced side effects. However, clinical DBS programming is typically done without the opportunity to visualize the spread of stimulation relative to the surrounding anatomy. In turn, current spread into non-target areas could occur without overt clinical signs, but still result in side effects not typically tested for in traditional clinical programming sessions. Therefore, recently developed Windows-based software tools that enable 3D visualization of the volume of tissue activated (VTA) by DBS as a function of the stimulation parameters and electrode location in the brain have been developed (Butson, C. R. et al., "StimExplorer: deep brain stimulation parameter selection software system," Acta Neurochir Suppl. 97, 569-74 (2007) (hereinafter "Butson et al., 2007b"); Miocinovic et al., 2007, the entire contents of each of which is hereby incoporated by reference herein). In an example embodiment, quantitative theoretical predictions are used to define stimulation parameter settings, customized to the patient, maximizing stimulation of target areas and minimizing stimulation spread to non-target areas.

Described herein is a comparison of the effectiveness of two DBS programming strategies, standard Clinical (where current is spread throughout the dorsal and ventral portions of the STN) and Model-based, on cognitive-motor performance in advanced PD patients under dual-task conditions, where the primary criterion for the selection of Model DBS parameters is maximizing stimulation of target areas in the subthalamic region while minimizing stimulation of associative/limbic (ventral) sections of the STN. The target areas were defined as the dorsal STN and white matter dorsal to the STN (FIG. 1) (Butson, C. R. et al., "Patient-specific analysis of the volume of tissue activated during deep brain stimulation," Neuroimage 34, 661-70 (2007) (hereinafter "Butson et al., 2007a"); Maks et al., 2009). Minimizing spread of current to the non-motor regions of the STN and focusing current spread to areas previously shown to produce ideal therapeutic benefit may minimize cognitive-motor declines under dual-task conditions without compromising improvements in motor function.

A total of 10 participants with advanced PD between the ages of 51 and 72 years (mean 58.6) participated in a study. Table 1 contains patient demographics and time since DBS surgery (DBS duration) and Table 2 contains Clinical and Model DBS parameters. All patients had undergone simultaneous bilateral STN DBS surgery at the Cleveland Clinic at least 14 months prior to study participation. Surgical procedures for DBS implantation have been reported in detail previously (Machado, A. et al., "Deep brain stimulation for Parkinson's disease: surgical technique and perioperative management," Mov. Disord. 21 Suppl. 14, S247-58 (2006), the entire contents of which is hereby incorporated by reference herein). Stimulation parameters for DBS devices were clinically determined using the methods described by Moro and colleagues (Moro et al., 2006) and were stable for at least six months prior to study participation. The programming of stimulators was overseen by an experienced DBS programming team consisting of a programming nurse and movement disorders neurologist specializing in PD. Because participants needed to make verbal responses during the working memory test, patients with dysarthria or speech impairment were excluded. Prior to data collection, all participants signed an informed consent approved by the Cleveland Clinic Institutional Review Board.

The N-Back Task

Various forms of the n-back task have been used in a number of previous studies (for comprehensive review see Owen, A. M. et al., "N-back working memory paradigm: a meta-analysis of normative functional neuroimaging studies," Hum. Brain Mapp. 25, 46-59 (2005), the entire contents of which is hereby incorporated by reference herein). The n-back task utilized in the current study was based on the methods originally used in its development. This version of the n-back task requires the participant to repeat the nth item back (e.g., 0-back, 1-back, 2-back) in a sequentially presented list of items (Dobbs, A. R. et al., "Adult age differences in working memory," Psychol Aging 4, 500-3 (1989), the entire contents of which is hereby incorporated by reference herein). This same technique was used in a recent dual-task study with advanced PD patients during unilateral and bilateral STN DBS (Alberts et al., 2008). The difficulty level of the n-back task is manipulated by requiring the participants to remember items further back in the list. The type of n-back test used in this study utilized a list of random letters presented to the participant. The number of intervening letters varied from zero to two. This method of n-back testing requires encoding, maintenance, updating and output. However, unlike other versions of the task it does not require comparison or decision-making.

Two English-speaking experimenters administered the n-back task. Experimenter 1 read aloud the randomized letter sets of the n-back task while experimenter 2 monitored the participant's responses for accuracy. Participants were

TABLE 1

Patient demographics and UPDRS-III scores during Off, Clinical and Model DBS conditions and the percent change from Off to Clinical and Off to Model DBS.

| | | | DBS | | | | UPDRS-III (%) | |
| | | Age | duration | UPDRS-III score | | | Off to | Off to |
| Patient | Gender | (years) | (months) | Off | Clinical | Model | Clinical | Model |
| --- | --- | --- | --- | --- | --- | --- | --- | --- |
| 1 | F | 52 | 14 | 61 | 32 | 35 | 47.54 | 42.62 |
| 2 | M | 51 | 40 | 65 | 30 | 40 | 53.85 | 38.46 |
| 3 | M | 54 | 26 | 50 | 31 | 31 | 38.00 | 38.00 |
| 4 | M | 63 | 38 | 56 | 35 | 32 | 37.50 | 42.86 |
| 5 | M | 71 | 29 | 61 | 26 | 30 | 57.38 | 50.82 |
| 6 | M | 53 | 17 | 44 | 26 | 18 | 40.91 | 59.09 |
| 7 | M | 72 | 35 | 51 | 31 | 29 | 39.22 | 43.14 |
| 8 | M | 51 | 33 | 55 | 30 | 27 | 45.45 | 50.91 |
| 9 | M | 61 | 45 | 68 | 28 | 31 | 58.82 | 54.41 |
| 10 | M | 58 | 14 | 56 | 31 | 32 | 44.64 | 42.86 |
| Mean | | 58.60 | 29.10 | 56.70 | 30.00 | 30.50 | 46.33 | 46.32 |
| SD | | 7.55 | 10.55 | 6.90 | 2.61 | 5.35 | 7.53 | 6.70 |

A 6 degree of freedom force-torque transducer (Mini-40 Model, ATI Industrial Automation, Garner, N.C., USA) was used to measure normal force (Fz; grip) during a force-tracking motor task. Grip force was measured with a resolution of 0.06 N at a sampling rate of 128 Hz. A customized LabView program developed by the inventors' laboratory was used to collect and display force data to the participant. In an example embodiment of the present invention, stimulation parameters may be selected based on results of a force-maintenance task test (e.g., in combination with a cognitive function test), where the force-maintenance task test is performed using a 6 degree of freedom force-torque transducer to measure the force. Moreover, the described resolution of 0.06 N may be used at the sampling rate of 128 Hz.

asked to respond by articulating the letter presented directly before (0-back), 1 cycle before (1-back), or two cycles before (2-back). If the participant provided an incorrect response or was unable to answer correctly within the allotted time (1.5 s) the trial would begin with a new sequence of letters. If the participant provides the correct answer, additional letters may be presented for the rest of the 30 second trial. Approximately 19-23 trials (letters) were presented during a 30 second block. After performing the n-back task for 30 seconds, participants rested for 15-45 seconds and then repeated the n-back task under the same level of difficulty (0, 1- or 2-back). Participants performed five 30 second blocks at each n-back condition (0, 1- and 2-back). These five blocks were collected sequentially and were randomized across participants. To account for practice effects, all participants completed three practice trials (30 seconds each) at each n-back level prior to data collection. Three trials have been shown to be sufficient to ensure task comprehension and stable performance for advanced PD patients (Alberts et al., 2008); all participants in the current study reported task comprehension and demonstrated stable performance. All practice and test blocks consisted of a unique list of randomized letters to prevent any memorization of letters. In an embodiment in which parameters are selected on a per-patient basis based on how the patient performs during the described tests, the n-back test may be administered and parameter selection may be based on number of total errors during 30 seconds, number of correct responses, and number of letters before the first error.

Force-Maintenance Task

Participants used a precision grip (i.e., thumb and index finger only) of their dominant hand to exert an isometric force against the force transducer. Similarly, in an example embodiment of the present invention, a precision grip may be used in a force maintenance test, based on results of which stimulation parameters are selected. The participant's dominant hand was determined using the Edinburg Handedness Inventory (Oldfield, R. C., "The assessment and analysis of handedness: the Edinburgh inventory," Neuropsychologia. 9, 97-113 (1971), the entire contents of each of which is hereby incoporated by reference herein). The force transducer was oriented in a comfortable position to the patient and affixed to the table to prevent any movement and for consistency throughout force tracking. Three maximum precision grip efforts, 5 seconds each, were completed at each of the three data collection sessions. These data were used to establish the maximum grip force of the patient. Between each maximum effort, patients rested 1-2 minutes. The peak force achieved from the three efforts was considered the maximum and was used to calculate a target force level; 20% of the maximum force. A target force level may similarly be selected for administering a test based on which to select stimulation parameters for a patient who performs the test. The 20% target force level was selected as Galganski and colleagues (Galganski, M. E. et al., "Reduced control of motor output in a human hand muscle of elderly subjects during submaximal contractions," J. Neurophysiol. 69, 2108-2115 (1993), the entire contents of which is hereby incorporated by reference herein) found no differences in younger adults' and older adults' standard deviation (SD) at this force level and based on previous studies with younger adults, older adults and advanced PD patients this force level could be maintained relatively easily with minimal fatigue (Alberts et al., 2008; Voelcker-Rehage, C., Alberts, J. L., "Age-related difference in working memory and force control under dual-task conditions," Aging, Neuropsychology, and Cognition 13, 1-19 (2006) (hereinafter "Voelcker-Rehage and Alberts, 2006"); Voelcker-Rehage, C. et al., "Effect of motor practice on dual-task performance in older adults," J. Gerontol B Psychol. Sci. Soc. Sci. 62, P141-8 (2007) (hereinafter "Voelcker-Rehage and Alberts, 2007"), the entire contents of each of which is hereby incorporated by reference herein). The target force level produced and actual real-time grip force produced by the participant was displayed on a 21" LCD monitor located ~44-59 cm directly in front of the participant. Participants were instructed to match their grip force to the target force line as accurately as possible. An auditory stimulus "ready, go" signaled the participants to start matching their force to the target force. Participants performed one to five practice repetitions prior to test blocks to be certain all task requirements were understood. Ten force-maintenance blocks for each limb, 30 seconds each, were performed with at least 30 seconds of rest between each block. The test administered to a patient for determining stimulation parameters for the patient, according to example embodiments of the present invention, may be similarly administered.

Dual Task: N-Back and Force Maintenance Simultaneously

Participants performed 15 dual-task blocks in which they were asked to simultaneously perform the n-back task and force maintenance task. The force maintenance task was performed in random combination with each of the three n-back conditions (0-back, 1-back, 2-back; five repetitions each). Participants were instructed to perform both tasks as accurately as possible and to devote half of their attention to the cognitive task and half of their attention to the motor task. Participants were given at least 30 seconds of rest between each block. The tests for selection of stimulation parameters on a per patient basis may be similarly administered.

Selection of Model DBS Parameters

For each subject enrolled in the study a patient-specific DBS computer model of each side of the patient's brain using Cicerone v1.2, a freely available academic DBS research tool (Miocinovic et al., 2007) (FIG. 1) was created. The models were created without any a priori knowledge of the patient, aside from access to their clinical MM and CT imaging data, surgical targeting data, and intra-operative microelectrode recording (MER) data. Researchers were blinded to each patient's clinical symptoms, drug regiment, clinical DBS programming notes, and Clinical stimulation parameter settings.

Each patient-specific DBS model included coupled integration of MRI/CT data, MER data, 3D brain atlas surfaces, DBS electrodes, and VTA predictions all co-registered into the neurosurgical stereotactic coordinate system following previously described methodology (FIG. 1) (Butson et al., 2007a; Butson et al., 2007b; Miocinovic et al., 2007, all of which are incorporated by reference herein). The first phase of model development was to import imaging data into the software. The stereotactic coordinate system was defined by identifying fiducial landmarks of the neurosurgical head frame used to implant the electrode (FIG. 1A). The CT or MRI acquired with the frame in place was called the frame image and any subsequent imaging data used in the model was co-registered to the frame image. Co-registration between the frame image and an alternative image was performed manually within Cicerone using a two step process. First, coordinates of the anterior and posterior commissures (AC/PC), defined by the operating neurosurgeon, were used to initially register the two images together. Second, a nine panel graphical user interface (GUI) allowed for manual manipulation to fine tune the image fusion. This GUI displayed the axial, coronal, and saggital views of the frame image on the left column, the alternative image on the right column and an overlay of the two in the middle column. Because the images were from the same individual a rigid body transformation could be performed to bring the images into near perfect alignment.

The second phase of model development consisted of entering the stereotactic location of each MER data point, color coded based on its neurophysiologically defined nucleus, into the model (FIG. 1B,C). 3D anatomical representations of the various nuclei of interest (thalamus, subthalamic nucleus, etc.) were then scaled and positioned within the context of the pre-operative MM and MER data (FIG. 1B,C). This process was performed manually, taking into account both anatomical structures visible in the MRI and fitting MER points within their respective nuclei, to provide the best possible overall fit of the brain atlas to the patient (Lujan, J. L. et al., "Automated 3-Dimensional Brain Atlas Fitting to Microelectrode Recordings from Deep Brain Stimulation Surgeries," Stereotact. Funct. Neurosurg. 87, 229-240 (2009); Maks et al., 2009). Once the patient's anatomical model was defined, the electrode type (Medtronic Electrode Model 3387 or 3389) was selected and the implantation position of the DBS electrode, as defined by intra-operative stereotactic coordinates, was displayed within the model system (FIG. 1D). Comparison with the post-operative CT verified that the intended surgical placement of the DBS electrode was within the artifact of the imaged electrode.

Figure 2:
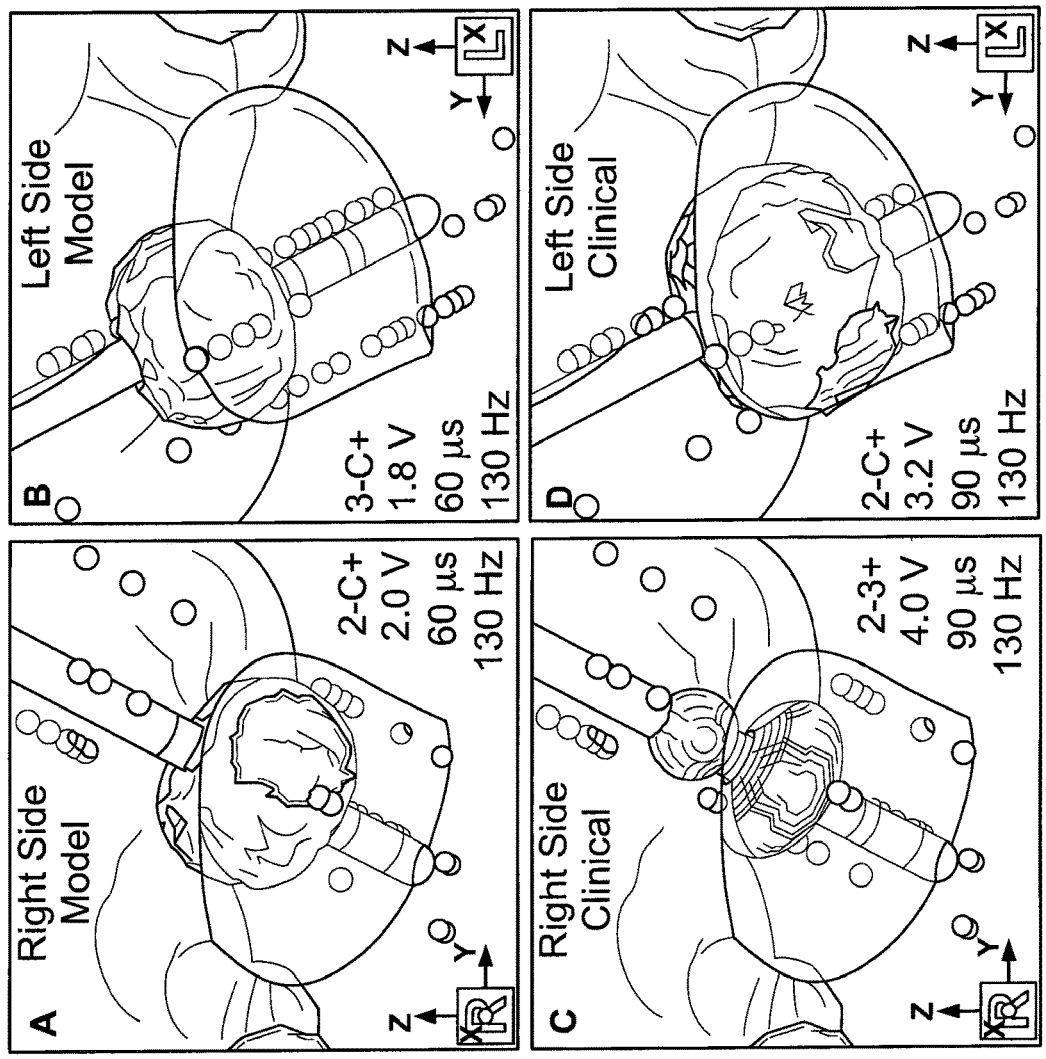
FIG. 2 shows a representative volume of tissue activated (VTA) for the Right and Left stimulators during Clinical and Model DBS settings referring to data presented for patient No. 1, where A) Right side Model settings: contact 2, 2.0V, 0.06 ms, 130 Hz, B) Left side Model settings: contact 3, 1.8 V, 0.06 ms, 130 Hz, and C) Right side Clinical settings: contact 2-3+, 4.0V, 0.06 ms, 130 Hz. D) Left side Clinical settings: contact 2, 3.2V, 0.06 ms, 130 Hz.

Based on previous experience developing patient-specific models of therapeutic STN DBS (Butson et al., 2007a; Maks et al., 2009), a theoretical ellipsoid target volume (FIG. 1E) was defined. Stimulation of this target area, which included the dorsal STN and white matter dorsal to the STN, has been associated with excellent clinical outcomes in previous work. A stimulation parameter setting was defined for each side of each patient's brain that maximized stimulation coverage of the target volume and minimized stimulation spread outside of the target volume. This theoretically optimal parameter setting was called the "Model DBS" and it was defined using theoretical predictions of the volume of tissue activated (VTA) (FIG. 2). The VTA provides an electrical prediction of the volume of axonal tissue directly activated by DBS for a given stimulation parameter setting. The VTAs used in Cicerone v1.2 are pre-compiled solutions from the DBS models previously described. (Butson, C. R. et al., "Predicting the effects of deep brain stimulation with diffusion tensor based electric field models," Medical Image Computing and Computer Assisted Intervention, International Conference on Medical Image Computing and Computer Assisted Intervention 9, 429-37 (2006) (hereinafter "Butson et al., 2006"), the entire contents of which is hereby incorporated by reference). The software provided the ability to quickly and interactively evaluate a wide range of stimulation parameter settings and enable definition of a theoretically optimal Model DBS for each side of each patient (Table 2).

TABLE 2

Clinical and model stimulation parameters for all patients

Left Stimulation Parameters

| | Clinical Settings | | | | Model Settings | | | |
|---|---|---|---|---|---|---|---|---|
| Patient | Contact | Voltage (V) | Pulse Width (µs) | Frequency (Hz) | Contact | Voltage (V) | Pulse Width (µs) | Frequency (Hz) |
| 1 | 2-C+ | 3.2 | 90 | 130 | 3-C+ | 1.8 | 60 | 130 |
| 2 | 2-C+ | 3.2 | 90 | 185 | 2-C+ | 2.6 | 60 | 130 |
| 3 | 2-3+ | 3.5 | 60 | 135 | 2-C+ | 2.3 | 60 | 130 |
| 4 | 2-3+ | 3.6 | 60 | 135 | 2-C+ | 1.8 | 60 | 130 |
| 5 | 2-3+ | 3.6 | 90 | 135 | 2-C+ | 2.6 | 60 | 130 |
| 6 | 2-C+ | 3.0 | 60 | 130 | 2-C+ | 2.4 | 60 | 130 |
| 7 | 1-3+ | 3.6 | 90 | 185 | 2-C+ | 2.5 | 60 | 130 |
| 8 | 1-C+ | 3.2 | 90 | 135 | 2-C+ | 2.4 | 60 | 130 |
| 9 | 1-2-C+ | 2.9 | 60 | 130 | 2-C+ | 1.8 | 60 | 130 |
| 10 | 1-C+ | 3.2 | 60 | 185 | 2-C+ | 2.4 | 60 | 130 |

Right Stimulation Parameters

| | Clinical Settings | | | | Model Settings | | | |
|---|---|---|---|---|---|---|---|---|
| Patient | Contact | Voltage (V) | Pulse Width (µs) | Frequency (Hz) | Contact | Voltage (V) | Pulse Width (µs) | Frequency (Hz) |
| 1 | 2-3+ | 4.0 | 90 | 130 | 2-C+ | 2.0 | 60 | 130 |
| 2 | 1-C+ | 3.6 | 60 | 185 | 2-C+ | 2.2 | 60 | 130 |
| 3 | 1-2+ | 3.5 | 60 | 135 | 2-C+ | 2.6 | 60 | 130 |
| 4 | 1-3+ | 3.3 | 60 | 135 | 2-C+ | 2.8 | 60 | 130 |
| 5 | 2-3+ | 3.9 | 90 | 135 | 2-C+ | 2.8 | 60 | 130 |
| 6 | 2-C+ | 3.2 | 60 | 130 | 2-C+ | 2.6 | 60 | 130 |
| 7 | 2-C+ | 3.6 | 90 | 185 | 3-C+ | 1.5 | 60 | 130 |
| 8 | 2-C+ | 3.2 | 60 | 135 | 2-C+ | 1.8 | 60 | 130 |
| 9 | 1-2-C+ | 2.9 | 60 | 130 | 2-C+ | 2.4 | 60 | 130 |
| 10 | 2-C+ | 3.2 | 60 | 185 | 2-C+ | 2.0 | 60 | 130 |

Following completion of the clinical study, the VTAs for each patient were quantified under both the Model and Clinical settings, along with their respective overlap with the STN volume. Each STN volume, as fitted to each hemisphere of each patient, was divided into a ventral and dorsal section. The STN division was defined by a plane parallel to the AC/PC plane that cut through the centroid of the STN. Table 3 contains the total VTA for each DBS condition and the percent in the ventral and dorsal portions of the STN (remaining numbers being outside the dorsal and ventral portions).

TABLE 3

Total volume of tissue activated (VTA) during Model and Clinical DBS and the percent of VTA within the dorsal and ventral portions of the STN for Model and Clinical settings.

| Patient | Side | Model | | | Clinical | | |
|---|---|---|---|---|---|---|---|
| | | total VTA | dorsal | ventral | total VTA | dorsal | ventral |
| 1 | Left | 45 | 13.8 | 0 | 116.6 | 47.4 | 18.9 |
| 1 | Right | 55.1 | 36.2 | 0.5 | 39 | 23.9 | 0 |
| 2 | Left | 71.7 | 20.3 | 0 | 108.9 | 31 | 0.6 |
| 2 | Right | 57.2 | 6.8 | 0 | 124.9 | 34.8 | 36.2 |
| 3 | Left | 65.4 | 28.2 | 2.3 | 29.1 | 12.3 | 0 |
| 3 | Right | 76.3 | 24.3 | 0.4 | 39.6 | 10.7 | 8.7 |
| 4 | Left | 49.6 | 25.7 | 0.3 | 29.8 | 15 | 0 |
| 4 | Right | 83.8 | 46.2 | 3.7 | 44.9 | 22.4 | 12.4 |
| 5 | Left | 76.4 | 38.9 | 6.4 | 33.6 | 19.5 | 0.2 |
| 5 | Right | 84.1 | 45.2 | 2.4 | 37.4 | 20.5 | 0 |
| 6 | Left | 68.4 | 22.1 | 0 | 96.9 | 32.3 | 0 |
| 6 | Right | 73.7 | 27.4 | 0.4 | 106.3 | 37.2 | 2.3 |
| 7 | Left | 68.9 | 13 | 0 | 45.3 | 4.2 | 6.3 |
| 7 | Right | 35.4 | 25.3 | 3.3 | 137.2 | 35.7 | 35.7 |
| 8 | Left | 68.2 | 17.5 | 0 | 129.1 | 28.2 | 28.5 |
| 8 | Right | 49.5 | 25.5 | 1.7 | 103.7 | 41.3 | 9.5 |
| 9 | Left | 47.4 | 12 | 0 | 199.9 | 78.8 | 33 |
| 9 | Right | 65.5 | 25.8 | 0 | 199.9 | 68.6 | 43.6 |
| 10 | Left | 64.5 | 21 | 0 | 106.3 | 39.5 | 37.7 |
| 10 | Right | 52.9 | 13 | 0 | 96.3 | 25.4 | 0 |
| AVERAGE | | 63.0 | 24.4 | 1.1 | 91.2 | 31.4 | 13.7 |
| STDEV | | 13.4 | 10.8 | 1.7 | 53.0 | 18.3 | 15.9 |

VTA (mm^3)

Calculation of Power Requirements for Stimulation Parameters

Waveforms were simulated according to the specific output of the Medtronic implanted pulse generator (Butson, C. R. et al., "Differences among implanted pulse generator waveforms cause variations in the neural response to deep brain stimulation," Clin Neurophysiol. 118, 1889-94 (2007) (hereinafter "Butson and McIntyre, 2007"), the entire contents of which is hereby incorporated by reference herein). The power of stimulation with a given frequency, pulse width, and amplitude was calculated by averaging the instantaneous power over a 1 second period, $$P_{ta} = \frac{1}{T} \int_0^T \frac{V(t)^2}{R} \cdot dt,$$

where Pta is the time-averaged power, T is set to 1 s, V(t) is the instantaneous voltage, R input resistance, and t is time. The power consumption, in microwatts, was calculated for Clinical and Model DBS settings.

Procedure

All data were collected during two visits to a research laboratory at the Cleveland Clinic. These two data collection sessions were separated by at least 72 hours. For both sessions, participants reported to the laboratory in the clinically defined off condition (i.e., at least 12 hours since their last dose of antiparkinsonian medication) while on DBS with their clinically defined stimulation parameters. After completing the informed consent process, patients were evaluated clinically with the Unified Parkinson's Disease Rating Scale (UPDRS) Part-III Motor Exam administered by an experienced movement disorders neurologist. The same neurologist completed all ratings except for one experimental session (patient 9; Clinical settings).

Each participant completed evaluation and testing under three DBS conditions: Off DBS, Clinical DBS, and Model DBS across the two laboratory visits. The order of testing Clinical and Model DBS parameters were randomized across patients across the two laboratory visits. For example, Day 1 testing consisted of completing all tests while on Clinical DBS and then following completion the patient's stimulator was turned Off for three hours and all clinical, motor, cognitive and cognitive-motor testing was repeated. On Day 2 the patient would complete all testing using the Model DBS parameters. Five patients were tested under Clinical DBS on Day 1 and five patients completed Model DBS on Day 1. Within each experimental session, the single task conditions were completed before the dual-task conditions. The single task conditions were the n-back task (three levels of difficulty: 0- 1- and 2-back) and force maintenance task only. The order of completing the single task cognitive and motor tasks was randomized across patients. The order of dual-task conditions, force maintenance with the three different levels of n-back, was randomized across patients.

According to the embodiment where stimulation parameters are selected on a patient-specific basis based on results of such tests, the tests may be performed initially under the stimulation settings of the predicted model parameters as discussed above. Subsequently, the tests may be performed under parameters selected based on the clinician's judgment in view of the patient's performance on prior iterations of test administration and VTA size and shape for various settings. Additionally, the tests may be administered and data may be collected prior to programming when the patient has yet to have any stimulation, to obtain a baseline of cognitive-motor function.

The Clinical DBS and Off DBS experimental session patients completed all testing on two occasions within the same day: first under Clinical DBS parameters and then while Off DBS. After completing all clinical, cognitive, motor and cognitive-motor tests under Clinical DBS, the patient's stimulators were turned Off for three hours to allow the effects of DBS to wear off (Alberts, J. L. et al., "Comparison of pallidal and subthalamic stimulation on force control in patient's with Parkinson's disease," Motor Control. 8, 484-99 (2004) (hereinafter "Alberts et al., 2004"); Alberts et al., 2008; Temperli, P. et al., "How do parkinsonian signs return after discontinuation of subthalamic DBS?," Neurolog. 60, 78-81 (2003), the entire contents of each of which is hereby incorporated by reference herein). During this three hour wash out period the patient remained in the laboratory and was provided lunch and rested. Following the 3 hour wash out period, the patient repeated all clinical, cognitive, motor and cognitive-motor tests. Upon completion of this experimental session, the patient's stimulators were turned on (Clinical DBS parameters were restored) and they resumed their antiparkinsonian medication. Approximately 30 minutes after taking their medication and restoration of DBS the patient departed the laboratory. The total time spent in the laboratory during a Clinical DBS and Off DBS experimental session was approximately 5-6 hours (~2 hours of data collection and 3 hours rest during the wash out period).

The Model DBS experimental session, which randomly occurred on Day 1 or Day 2, was completed in approximately 4-5 hours. For the Model DBS session, the patients arrived in the laboratory off antiparkinsonian medication and on Clinical DBS. Upon arrival, both stimulators were turned Off. The patient then rested in the laboratory for the next two hours. After two hours the patient was re-programmed using the Model DBS parameters. After 60 minutes under Model DBS parameters, the patient completed all clinical, cognitive, motor and cognitive-motor testing. Upon completion of the Model DBS testing session, the patient's stimulators were reprogrammed to their clinically defined parameters and they took their anti-parkinsonian medication and departed the lab approximately 30 minutes later.

Data Analysis

Force-maintenance: All force data were filtered with a phase-symmetric low-pass filter employing Woltring's algorithm (detailed in previous studies (Voelcker-Rehage, C., Stronge, A. J. et al., "Age-related differences in working memory and force control under dual-task conditions," Neuropsychol. Dev. Cogn. B Aging Neuropsychol. Cogn. 13, 366-84 (2006) (hereinafter "Voelcker-Rehage et al., 2006"); Voelcker-Rehage and Alberts, 2007)) using existing Matlab analysis programs developed in the inventors' laboratory. Force data were assessed to determine the patients' accuracy from three seconds after the start of the block until completion of the block; this period allowed the patient sufficient time to achieve the target force. That is, test results were collected beginning after three seconds. The primary motor outcome variables for the force-tracking task were time within the target range (TWR) and relative root mean square error (RRMSE). The TWR is calculated by determining the time the patient's force trace is within ±2.5% of the target line, i.e. within 2.5% of the force, such that, for example, if the target force is 5N, the TWR is the time at which a force is maintained in the range of 4.375-5.625N. This may be different for each patient, based on the patient's target force. The assessment was done after the data collection so the patient was not targeting this region specifically. The TWR provides an overall accuracy measure of force-tracking. To account for differences in the amplitude of the target force (e.g., inter-patient and intra-patient variability due to stimulation status), the RRMSE, as defined in equation 1, was used as a method of normalizing performance relative to force amplitude. The RRMSE is considered to reflect the overall variability of force-tracking performance; a lower RRMSE suggests control of distal musculature and hand functionality (Kriz, G. et al., "Feedback-based training of grip force control in patients with brain damage," Arch. Phys. Med. Rehabil. 76, 653-659 (1995); Kurillo, G. et al., "Force tracking system for the assessment of grip force control in patients with neuromuscular diseases," Clin. Biomech (Bristol, Avon) 19, 1014-21 (2004), the entire contents of each of which is hereby incorporated by reference herein). In the equation below, $F_T(t)$ is the target force provided to the patient, $F_0(t)$ is the force produced by the patient and T is the time of the block.

$$RRMSE = \sqrt{\frac{1}{T}\sum_{t=0}^{T}\frac{(F_0(t)-F_T(t))^2}{\max(F_T)^2}}$$

TWR and RRMSE may be used according to the embodiment where test results are used for selection of parameters on a patient specific basis. Greater TWR reflects better performance and lower RRMSE reflects better performance.

N-back performance: N-back performance was measured by determining the percentage of correct letters recalled during a 30 second block and the total number of errors committed during a block (Voelcker-Rehage et al., 2006).

Dual-task Analysis: To examine participants' performance under the dual-task conditions, the dual task loss (DTL) was computed using a standard measure to compare performance on single and dual-task conditions (Lindenberger, U. et al., "Memorizing while walking: increase in dual-task costs from young adulthood to old age," Psychol. Aging 15, 417-436 (2000), the entire contents of which is hereby incorporated by reference herein). The DTLs were computed as the percentage of loss in motor and cognitive performance during dual-task conditions relative to performance in the single-task conditions in the following manner:

$DTL_{force}$[(mean dual-task$_{force}$−
mean baseline$_{force}$)/mean baseline$_{force}$]×100.

$DTL_{n\text{-}back}$=[(mean dual-task$_{n\text{-}back}$−
mean baseline$_{n\text{-}back}$)/mean baseline$_{n\text{-}back}$]×100.

This is a measure that essentially determines the cost from a motor and cognitive perspective of moving from a single task to the more complex and difficult dual-task.

Statistical Analysis

Motor (RRMSE, TWR) and cognitive (percentage of correctly repeated letters (PRL), number of errors (NE)) performance data were analyzed with repeated measures ANOVAs (analysis of variance). Greenhouse Geyser adjustment was reported when the sphericity assumption was violated. Post-hoc contrasts (Bonferroni adjustment) were used to determine differences between the DBS status and level of task difficulty to determine the conditions that were most affected by the different DBS parameter settings. Analyses were conducted separately for the motor and cognitive task. These statistical methods may be applied according to the embodiment in which parameters are selected based on the test results.

Two 3 (DBS condition: Off DBS, Clinical DBS, Model DBS)×3 (task difficulty: 0-back, 1-back, 2-back)×2 (context: single-task, dual-task) repeated measure ANOVAs were used to determine differences between different DBS parameter settings in n-back difficulty and between single- and dual-task context using PRL and NE. The repeated measure ANOVAs may be used when the study design is a within subject repeated measure, such that multiple measures on the same patient are obtained, but under varying conditions. Additionally, two 3 (DBS condition)×4 (task difficulty: force only, force at 0-back, 1-back, and 2-back difficulty) repeated measure ANOVAs were carried out using the RRMSE and TWR scores.

To examine whether DTLs for the force maintenance task and the n-back difficulties were significantly different from zero, a series of one-sample t tests (test value=0) were conducted separately for each DBS condition. Repeated measures ANOVAS with corresponding post-hoc tests were used to compare the DTLs for task difficulties (0-back, 1-back, 2-back) and DBS status. If there is no cost in moving from a single to a dual task, then the DTL would be zero.

Results

Clinical Ratings

Table 1 contains UPDRS-III Motor scores for each patient during Off, Clinical, and Model DBS. For all patients, the UPDRS-III scores decreased (and lower is better) with Clinical and Model DBS compared to Off DBS. Clinical DBS, on average, resulted in a 46 percent improvement in UPDRS-III ratings (range: 37 to 58 percent) while Model DBS also improved clinical UPDRS-III ratings by 46 percent (range: 38 to 59 percent). Statistical analysis (t-tests for paired samples) revealed that UPDRS-III scores for Clinical and Model DBS were significantly better than Off DBS (tcli-off(9)=3.90, p=0.004; tmod-off(9)=3.30, p=0.009). However, there was no statistical difference in UPDRS-III scores between Clinical and Model DBS settings (t(9)=0.23, p=0.820).

DBS Power Consumption

The power consumption associated with Clinical and Model parameters for each stimulator and the total amount of power, in microwatts, is provided in Table 4. In terms of total power consumption, the Model parameters consume approximately 50 percent less microwatts than Clinical parameters ($t_{mod-cli}(9)=8.45$, p<0.0001). For all 10 patients, total power consumption was less with Model compared to Clinical parameters and power consumption was less with Model compared to Clinical parameters for both the right and left stimulators.

Cognitive Functioning and DBS During Single and Dual-task Conditions

Figure 3:
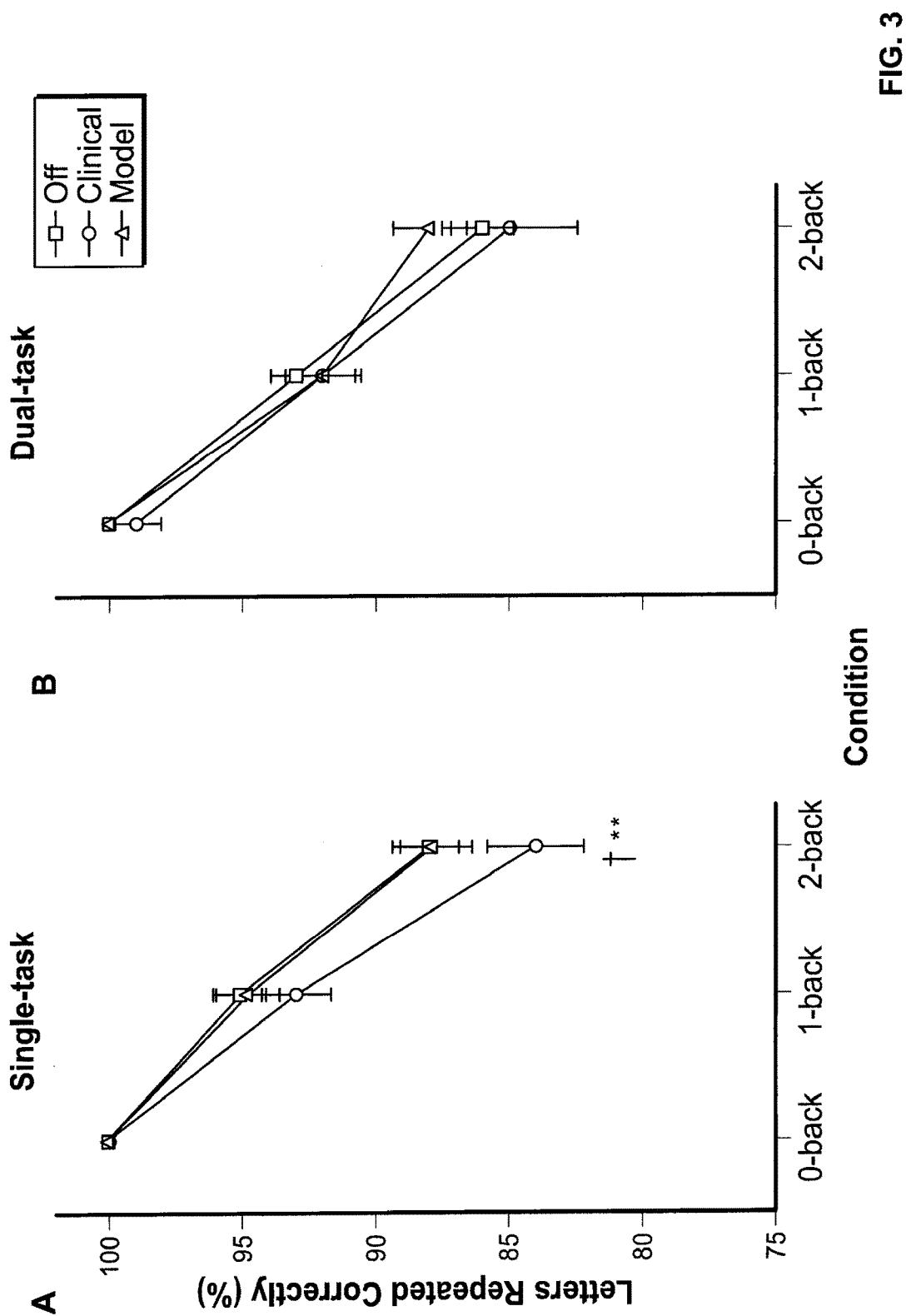
FIG. 3 illustrates working memory performance as percent of letters correctly repeated during single- and dual-task conditions, pertaining to (A) results of the n-back task in the single-task condition at Off DBS, Clinical DBS and Model DBS (Means and Standard Errors), and (B) results of the n-back task in the dual-task condition at Off DBS, Clinical DBS and Model DBS (Means and Standard Errors), and where a cross marks a significant differences between Off and Clinical DBS, an asterisk marks a significant difference between Off and Model DBS, and a double asterisk marks a significant difference between Clinical and Model DBS.

Percentage of Correct Letters (PCL): The results from the repeated measures ANOVA (cf. FIG. 3) revealed that overall n-back performance decreased with increasing task difficulty (F(2, 18)=48.422, p<0.001, $\eta^2$=0.843). The main effects of DBS status (F(2, 18)=2.010, p=0.163) did not achieve statistical significance while the main effect of context (F(2, 18)=4.879, p=0.055) approached statistical significance. The task difficulty×DBS condition interaction, however, was significant (F(4,18)=2.945, p=0.033, $\eta^2$=0.247), resulting from a greater performance decrease with increasing n-back difficulty for Clinical DBS than for Off and Model DBS. Performance on the 2-back during Clinical DBS was significantly lower than performance at Off DBS or Model DBS in single-task conditions. As task difficulty increases as a result of an increase in cognitive demands of the dual-task performance, declines would be found during Clinical DBS, but not during Model DBS.

Number of Errors (NE): Errors in cognitive function were primarily due to responding with the incorrect letter and the participant reporting to experimenter that they did not remember the letter to be recalled. Less than 0.5 percent of the errors were the result of the patient not responding within the ~1.5 second time period. For the number of errors, the effect of task difficulty (F(2, 18)=50.381, p<0.001, $\eta^2$=0.848) and the task difficulty by context interaction (F(2, 18)=3.859, p=0.040, $\eta^2$=0.300) were significant. Participants produced more errors as the difficulty of the n-back task increased. The number of errors, however, did not significantly differ between the DBS states (F(2, 18)=0.450, p=0.644). This can occur, for example, as a function of the number of letters presented. For example someone can perseverate on a response and not get as many letters presented to that person.

Motor Function and DBS During Single and Dual-task Conditions

Figure 4:
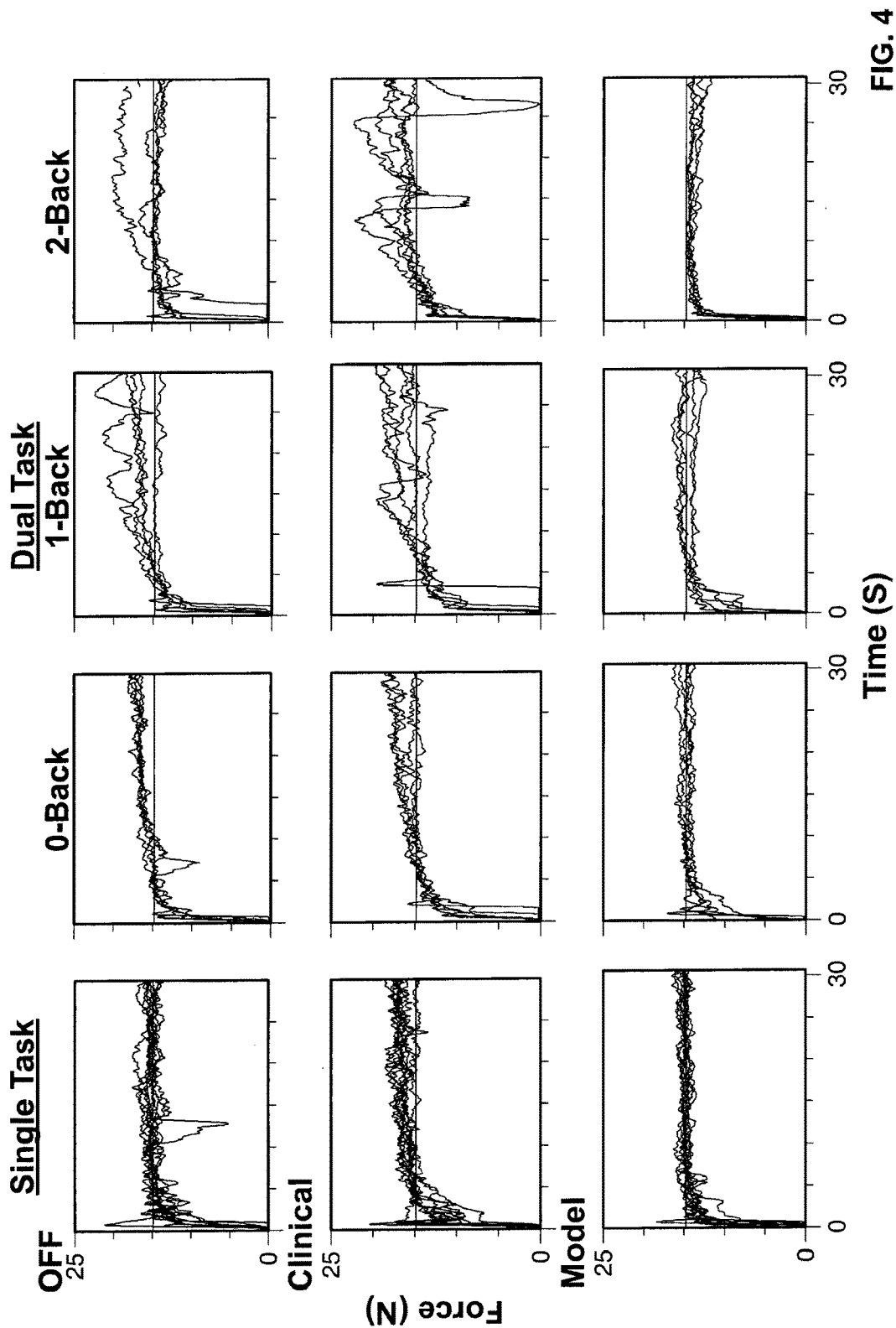
FIG. 4 shows representative force-tracking trials (pertaining to patient 1) during Single (left-most column) and all Dual-task conditions (right columns) under the three DBS settings: Off (upper plots), Clinical DBS (middle plots) and Model DBS (lower plots), where the horizontal line represents the target force line the patient was instructed to match.

Representative force-tracking data for an entire set from one patient for all three DBS conditions during single and dual-task settings are presented in FIG. 4. When performing the force-tracking task only (left plots), Clinical and Model DBS resulted in better tracking performance compared to Off DBS.

While patients were Off, force tracking performance became slightly more variable as the difficulty of the dual-task increased. During Clinical DBS, middle plots, force-

TABLE 4

Power consumption, in microwatts, for Clinical and Model stimulation parameters for each side and total power requirements for Clinical and Model parameters.

| | Power (μW) | | | | | |
|---|---|---|---|---|---|---|
| | Clinical | | Model | | Total | |
| Patient | Left | Right | Left | Right | Clinical | Model |
| 1 | 122.65 | 191.63 | 25.67 | 31.69 | 314.28 | 57.36 |
| 2 | 174.53 | 146.13 | 53.56 | 38.35 | 320.66 | 91.91 |
| 3 | 100.79 | 100.79 | 41.91 | 53.56 | 201.58 | 95.47 |
| 4 | 106.63 | 89.60 | 25.67 | 62.12 | 196.24 | 87.79 |
| 5 | 161.19 | 189.18 | 53.56 | 62.12 | 350.37 | 115.68 |
| 6 | 71.31 | 81.13 | 45.64 | 53.56 | 152.44 | 99.20 |
| 7 | 220.89 | 220.89 | 49.52 | 17.83 | 441.79 | 67.35 |
| 8 | 127.36 | 84.25 | 25.67 | 45.64 | 211.62 | 71.31 |
| 9 | 66.63 | 66.63 | 25.67 | 45.64 | 133.27 | 71.31 |
| 10 | 115.46 | 115.46 | 45.64 | 31.69 | 230.92 | 77.33 |
| Mean | 126.75 | 128.57 | 39.25 | 44.22 | 255.32 | 83.47 |
| SD | 47.43 | 54.77 | 12.21 | 14.39 | 97.70 | 17.62 | tracking performance declined dramatically as task difficulty increased, in particular during the 2-back condition in which variability was greatest. The lower panels depict force-tracking trials during Model DBS. In general, the consistency of force tracking was relatively unaffected by increasing task difficulty under dual-task conditions. The TWR and RRMSE measures were used to quantify force-tracking performance.

Figure 5:
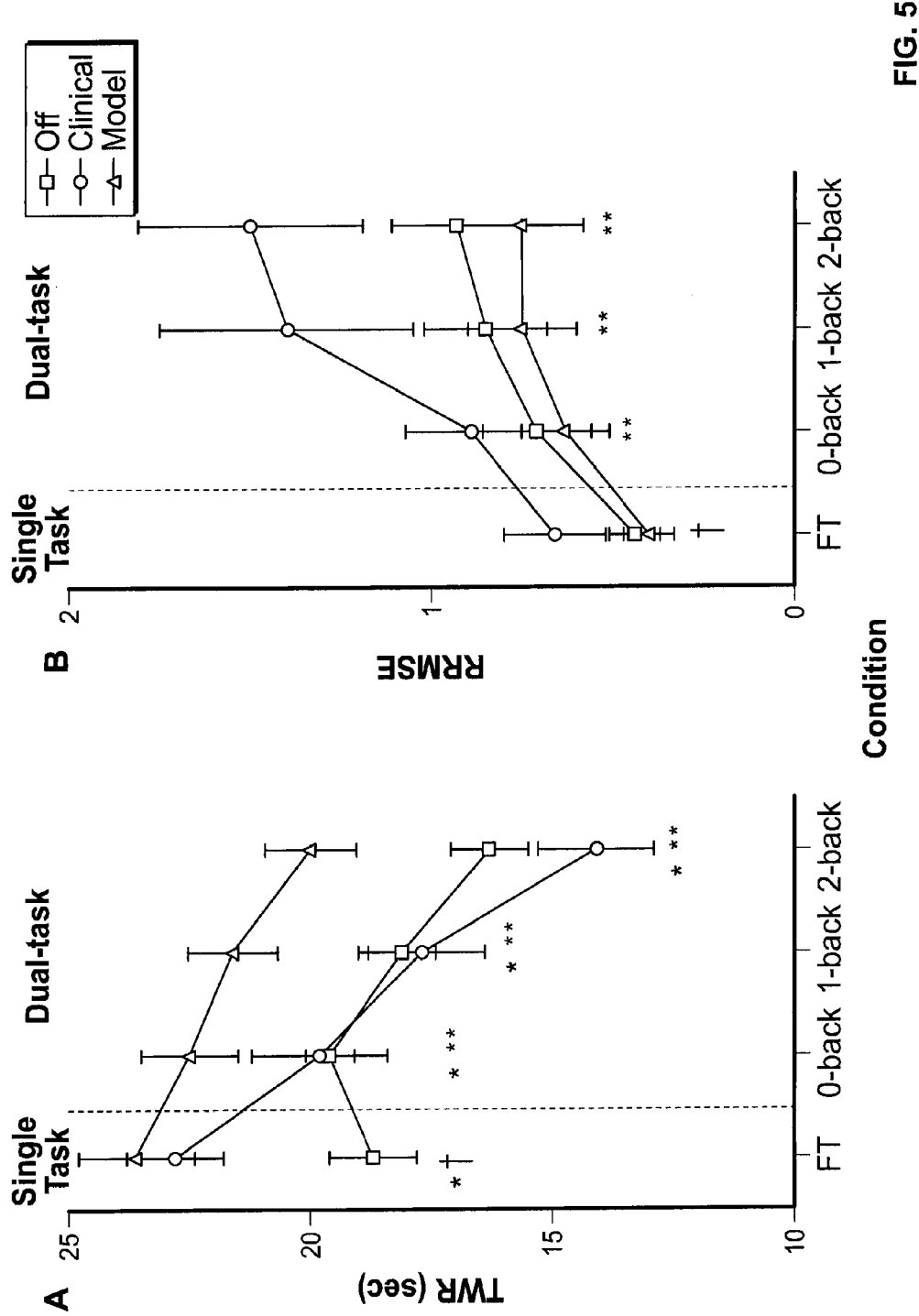
FIG. 5 shows force-tracking performance across stimulation conditions, where (A) results of the time within the target range (TWR) of force in the Single and Dual-task conditions at Off DBS, Clinical DBS and Model DBS (Means and Standard Errors), and (B) results of the relative root mean square error (RRMSE) force in the single and dual-task conditions at Off DBS, Clinical DBS and Model DBS (mod DBS) (Means and Standard Errors), and where a cross marks a significant differences between Off and Clinical DBS, an asterisk marks a significant difference between Off and Model DBS, and a double asterisk marks a significant difference between Clinical and Model DBS.

Time within Target Range (TWR): When completing the force maintenance task only, Clinical and Model DBS conditions were significantly better than the Off DBS condition. As expected, motor performance tended to decrease (lower TWR) as patients moved from the single to dual-task conditions (cf FIG. 5a). However, the rate of decline in motor performance differed across stimulation conditions. With Clinical DBS the rate of motor performance decline was greater compared to the decline under Model DBS settings. A significant interaction between DBS condition and task difficulty was present (F(6,54)=4.857, p<0.001, $\eta^2$=0.351). During Off and Model DBS conditions, the slope of decline in motor performance was similar across dual-task conditions. However, under Clinical DBS settings, TWR decreased dramatically across all task difficulties. Furthermore, Model DBS led to significantly better force tracking performance as compared to Clinical DBS or Off DBS in all dual-task conditions.

Relative root mean square error (RRMSE): In general, the variability in force tracking increased significantly as task difficulty increased, moving from single to dual-task conditions (F(1.35,27.73)=10.113, p=0.005, $\eta^2$=0.529). Additionally, the force variability differed between the three DBS conditions (F(2,54)=5.042, p=0.018, $\eta^2$=0.359), and the greatest variability occurred under Clinical DBS. In the dual-task conditions, Clinical DBS resulted in significantly worse performance than Off and Model DBS (cf. FIG. 5b). As shown in FIG. 5b, Clinical DBS resulted in more variable force production across conditions; as task difficulty increased to the 2-back condition, force variability was significantly greater compared to Model DBS.

Dual-task losses (DTLs) different from zero: The DTLs for n-back performance at the 0-back condition were relatively small and non-significant across the three DBS testing conditions. Declines in n-back performance were greater when moving from the single task 1-back condition to the dual-task 1-back condition, in particular for the Off DBS and Model DBS conditions (due to the fact that under single task conditions n-back performance was relatively high). In study data, the DTLs associated with Clinical DBS were not significantly different from the DTLs associated with Model DBS. From a cognitive perspective, the cost in performance when moving from single- to dual-task conditions was not statistically significant for any of the stimulation conditions. A reason for this may be that, despite the fact that patients reported attending to both tasks equally, they may have placed greater emphasis or allocated more attentional resources to performing the working memory task compared to force-tracking.

Figure 6:
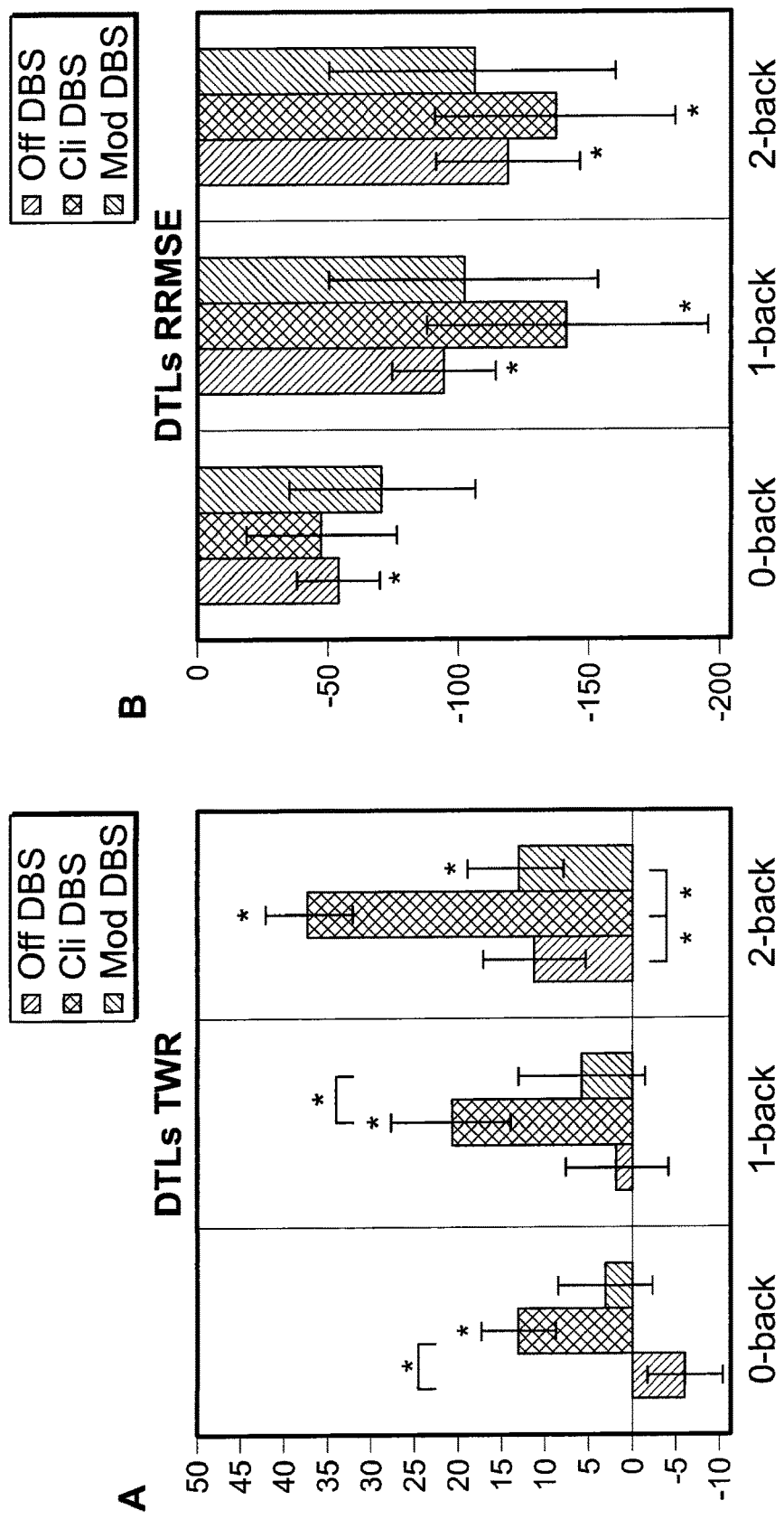
FIG. 6 shows dual-task losses (DTLs) and standard errors for (a) the force maintenance task (TWR), and (b) RRMSE at Off DBS, Clinical DBS (cli DBS), and Model DBS (mod DBS), where an asterisk signifies DTLs significantly greater then zero and significant differences between the states of stimulation ($*p<0.05$).

As expected, force tracking performance did decline as task complexity increased from single to dual-task conditions while Off DBS and under Clinical and Model DBS settings. However, the declines in force tracking, FIGS. 6a and 6b, were most present during Clinical DBS settings. For TWR, the greatest declines in motor performance when moving from a single to dual-task conditions were associated with Clinical DBS (Clinical DBS: $t_{0-back}(9)$=3.091, p=0.013; $t_{1-back}(9)$=3.058, p=0.014; $t_{2-back}(9)$=7.151, p<0.001; Model DBS: $t_{0-back}(9)$=0.537, p=0.604; $t_{1-back}(9)$=0.771, p=0.460; $t_{2-back}(9)$=2.363, p=0.042; Off DBS: $t_{0-back}(9)$=−1.542, p=0.157; $t_{1-back}(9)$=0.269, p=0.794; $t_{2-back}(9)$=2.026, p=0.073). The greatest performance decrements for each DBS condition occurred during the most complex testing condition, 2-back+force maintenance (compared to just force maintenance without the n-back test), and the smallest decrement during the simplest, 0-back+force maintenance (cf. FIG. 6a) (compared to just force maintenance without the n-back test). That is, as complexity of the task is increased, the quality of performance decreases, A similar pattern of results was present when examining the variability of force production (RRMSE): $t_{0-back}(7)$=3.54, p=0.01; $t_{1-back}(7)$=3.33, p=0.01; $t_{2-back}(7)$=7.42, p<0.01) (cf. FIG. 5b). The greatest declines in motor performance were associated with Clinical DBS ($t_{0-back}(9)$=−1.674, p=0.128; $t_{1-back}(9)$=−2.636, p=0.027; $t_{2-back}(9)$=−2.970, p=0.016). The DTLs in force tracking performance (RRMSE) at Off DBS were significant for all n-back conditions ($t_{0-back}(9)$=−3.767, p=0.004; $t_{1-back}(9)$=−5.023, p=0.001; $t_{2-back}(9)$=−4.131, p=0.003), whereas under Model DBS DTLs were not significant ($t_{0-back}(9)$=−2.014, p=0.075; $t_{1-back}(9)$=−2.005, p=0.076; $t_{2-back}(9)$=−1.924, p=0.087).

Task Difficulty and Stimulation Differences in DTLs: The $DTLs_{n-back}$, in general, increased significantly as task difficulty also increased, (F(2, 18)=3.831, p=0.041, $\eta^2$=0.299). However, the $Das_{n-back}$ were not differentially affected across stimulation conditions (Off, Clinical or Model) (F(2, 18)=0.425, p=0.660).

For the $DTLs_{force}$, a significant main effect of task difficulty for TWR was present (F(2, 18)=26.984, p<0.001, $\eta^2$=0.750). As task difficulty increased, DTLs in force maintenance also increased as shown in FIG. 6a. The loss in motor performance was relatively small for the 0-back condition while relatively large for the 2-back dual-task condition. A significant main effect of stimulation (F(2, 18)=5.940, p=0.010, $\eta^2$=0.398) was present. Differences between DBS states were significant in the 0-back, 1-back and 2-back conditions (significantly higher DTLs with Clinical DBS compared to Off and Model DBS). The DTLs in terms of the variability (RRMSE) of force production were similar to TWR as losses in performance were greater during Clinical compared to Off and Model DBS conditions (FIG. 6b).

DISCUSSION

Recently, it has been shown that bilateral STN DBS disrupts PD patients' cognitive-motor functioning under dual-task conditions (Alberts et al., 2008). These DBS related declines in cognitive-motor functioning are minimized through the use of patient-specific DBS models that account for electrode location and the VTA. In an example embodiment, the primary criterion for the selection of DBS parameters may be maximized stimulation coverage of a target volume that includes the dorsal STN and white matter dorsal to the STN, thus minimizing stimulation of non-motor regions of the STN.

The typical clinical method of DBS programming was compared, with respect to cognitive-motor performance in advanced PD patients, to the computational approach described herein for selecting DBS parameters that minimize stimulation of non-motor regions of the STN. Clinical assessments indicated both methods of DBS programming were effective in improving UPDRS-III scores. However, under all dual-task conditions motor performance was, in general, better with Model determined stimulation parameters compared to Clinical settings. In addition, cognitive performance (working memory) was better during modestly complex task conditions, using Model compared to Clinical settings. Overall, these data suggest that cognitive-motor declines associated with bilateral STN DBS can be mitigated through the use of software that depicts the VTA associated with a given parameter setting relative to the targeted brain structure.

Figure 7:
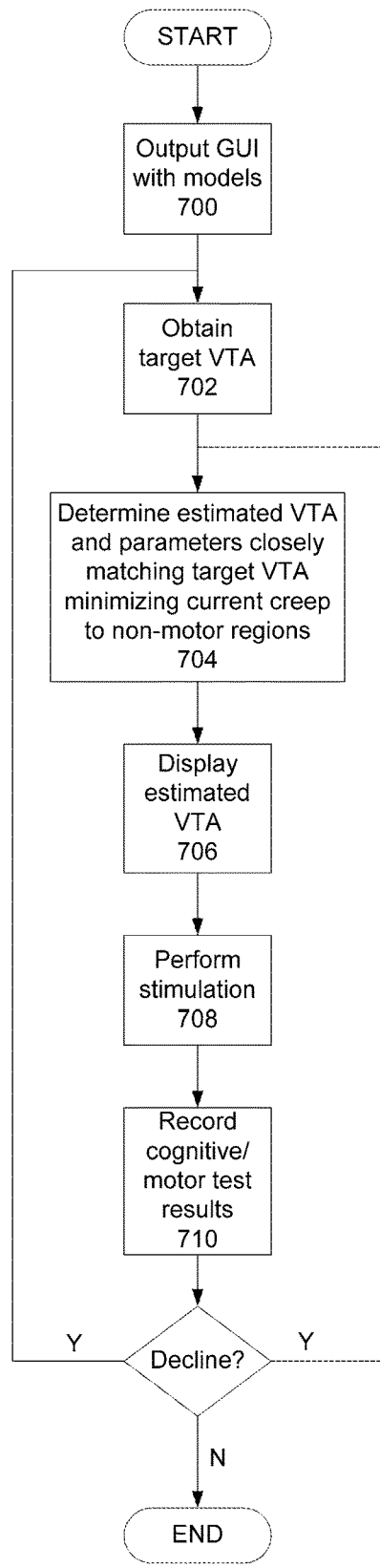
FIG. 7 is a flowchart showing a stimulation parameter selection method, according to an example embodiment of the present invention.

Referring to FIG. 7, in an example embodiment of the present invention, a system may, at step 700, output a GUI including a display of a model of a patient anatomy, e.g., the patient's brain, co-registered with a model of a stimulation leadwire. The brain model may be generated, for example, by fitting a brain atlas to images of the patient's brain. Alternatively, the images themselves may be displayed. Alternatively, the system may display the images and the model co-registered with each other.

At step 702, the system may obtain user input identifying a target VTA. The target VTA may be drawn such that it does not include more than 10% of the non-motor region of the patient brain, and specifically less than 10% of globus pallidus. In an example, the target VTA may be drawn such that it does not include any of the non-motor region.

At step 704, the system and method may determine an estimated VTA and corresponding stimulation parameters whose stimulation is estimated to produce the estimated VTA, which estimated VTA most closely matches the obtained target VTA. In an example embodiment, the estimated VTAs (and corresponding stimulation parameters) from which the system may select may be limited to those that do not extend outward beyond any of the perimeter of the target VTA, such that if the closest estimated VTA extends beyond the target VTA, a VTA that is less of a match but is completely included within the area of the target VTA would be selected. The estimated VTAs may be calculated based on predetermined functions and/or based on a patient population as further described in the '330, '312, '340, '343, and '314 applications.

In an alternative example embodiment, the system may be initially configured with a universal target VTA drawn to the generic model which is then mapped to the specific patient, separate input of a target VTA for each patient not being necessary. The system may provide a patient-specific closest matching estimated VTA and associated stimulation parameters based on the universal target VTA as applied to the patient model and based on a currently used electrode leadwire.

The clinician may use the output parameters for bilateral DBS stimulation for the patient. Because the parameters correspond to an estimated VTA that closely matches the target VTA which does not include stimulation of non-motor regions, or at least only up to 10% of such regions of the brain, and specifically less than 10% of globus pallidus, there would be significant improvement with respect to cognitive and/or motor-cognitive degeneration as compared to conventional bilateral DBS stimulation.

At step 706, the system and method may display the estimated VTA overlaid on the patient brain/leadwire model. For example the system may remove the target VTA from display, the estimated VTA being displayed in its place.

In an example embodiment of the present invention, cognitive, motor, and cognitive-motor function of the patient may be assessed to fine tune the stimulation parameters. For example, at step 708, the stimulation parameters corresponding to the estimated VTA may be used in a stimulation of the patient brain. Instead of the stimulation parameters corresponding to the estimated VTA, the system may allow for the clinician to provide input to modify the stimulation parameters, e.g., directly or by shifting the displayed estimated VTA or a displayed current field.

While the patient undergoes such stimulation, motor and cognitive tests, e.g., the combination of the n-Back test and the force-maintenance task as described above, may be administered. The system, at step 710, may record results of such tests. For example, the system may record and/or calculate the data corresponding to the graphs shown in FIGS. 3-6. With respect to force-maintenance, the system may include a force sensor that senses the force exerted by the patient, and may record such figures and determine the difference of such sensed force to a target force. The system may also output audio through a speaker listing a series of letters and may receive speech input via a microphone repeating letters for the n-back test. The system may compare the speech input to recorded letters that had been output to determine the correctness of the speech input. Alternatively, a clinician may administer the tests, e.g., offline.

If the results show a decline in motor, cognitive, and/or motor-cognitive function, the clinician may input a new target VTA, so that the method returns to step 702. Otherwise, the method may end.

In an example embodiment, the system may be preconfigured with predefined metrics concerning results of the administered tests, indicating acceptable results and unacceptable results. For example, the system may be configured with such indications concerning TWR, RRMSE, and DTLs with respect to motor and/or cognitive skill as appropriate. In response to unacceptable results, the system may (as reflected by the broken lines) automatically cycle back to, for example, step 704 to determine a new set of parameters and associated estimated VTA which may improve such patient functions. For example, the system may select parameters that produce a VTA with less stimulation of non-motor regions of the brain or whose edges are further from such regions of the brain.

According to an example embodiment, the system and method may record and visually identify which explored VTAs were associated with a side effect. The clinician may identify a VTA for which there are subpar results of the described tests as such VTAs. Additionally or alternatively, the system may automatically record such VTAs as being associated with a side effect.

Such recordation may be helpful in that, for example, the system may output a GUI showing explored regions and indicate which of those have been associated side effects, so that the clinician has more information on which to base selection of stimulation parameters during subsequent stimulation sessions.

In an example embodiment of the present invention, after determining the stimulation parameter settings, e.g., based on automatic or manual selection of parameters corresponding to a VTA that is closest to a target VTA that avoids the non-motor regions of the brain, and or based on results of motor function, cognitive function, and dual motor-cognitive function tests, a voltage of an electrode may be decreased if a selected voltage is determined to cause a tingling sensation in the patient stimulated with the determined stimulation parameters.

While is has been reported that when memory demands of a task were increased, PD patients with bilateral STN DBS exhibited deficits in working memory (Hershey et al., 2004), it has been determined that unilateral STN DBS has little effect on working memory as n-back performance was similar during unilateral stimulation to that when patients were off DBS (Alberts et al., 2008). In the current study, with respect to bilateral STN DBS, n-back performance at the most difficult condition (2-back) was compromised to a greater degree under Clinical DBS than under Model DBS or when Off DBS. These data suggest that minimizing current spread to the non-motor regions of the STN may alleviate some of the declines in working memory that may be associated with bilateral STN DBS. While the use of Model parameters did mitigate working memory declines, compared to Clinical parameters, working memory during bilateral STN DBS with Model parameters was not better than performance during unilateral STN DBS (Alberts et al., 2008). The observation that cognitive functioning (working memory) during unilateral DBS was better than bilateral STN DBS, whether Model or Clinical based, provides a rationale for taking a more conservative approach to the implantation of DBS systems.

Therefore, according to an example embodiment of the present invention, a stimulation method may include implementing a staged DBS implantation strategy, by initially performing unilateral DBS, assessing the impact of the unilateral DBS, e.g., on cognitive function, and subsequently implanting the second side. Such a method may decrease the likelihood of cognitive declines that can be associated with bilateral STN DBS and which may ultimately diminish the patient's overall quality of life. For example, the unilateral DBS may be determined to be sufficiently effective, and the bilateral DBS may be delayed for 6-12 months or even as long as 5 years. thereby delaying the increased cognitive impairment that is a result of the bilateral DBS.

In the event of inconsistent usages between this document and those documents incorporated by reference herein, the usage in the incorporated reference(s) should be considered supplementary to that of this document; and for irreconcilable inconsistencies, the usage in this document controls.

The above description is intended to be illustrative, and not restrictive. Those skilled in the art can appreciate from the foregoing description that the present invention may be implemented in a variety of forms, and that the various embodiments may be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and following claims. For example, while example embodiments discussed in detail refer to PD patients, embodiments of the present invention, for example, pertaining to selection of stimulation parameters based on monitoring of cognitive function, motor function, and combination thereof, may be applied to patients having other neuro-degenerative diseases, including neuro-motor diseases or neuro-cognitive diseases.

What is claimed is:

1. A method for treating a neurological disorder that results in abnormal motor function, the method comprising:
    determining, by a computer processor, an estimated volume of tissue activated (VTA) using a set of stimulation parameters, wherein the estimated VTA comprises at least a portion of at least one of the zona incerta, lenticular fasciculus, or motor region of the globus pallidus and the estimated VTA comprises less than 10% of non-motor anatomical-neural regions of a subthalamic nucleus;
    providing the set of stimulation parameters to a deep brain stimulation device comprising a leadwire and a plurality of electrodes disposed along the leadwire; and
    stimulating the portion of the at least one of the zona incerta, lenticular fasciculus, or motor region of the globus pallidus using the deep brain stimulation device and the set of stimulation parameters.

2. The method of claim 1, further comprising obtaining, by the computer processor, a target volume of tissue activated (VTA), wherein the target VTA comprises less than 10% of the non-motor anatomical-neural regions of the subthalamic nucleus, wherein the target VTA comprises at least a portion of at least one of the zona incerta, lenticular fasciculus, or motor region of the globus pallidus.

3. The method of claim 2, wherein obtaining the target VTA comprises receiving, by the computer processor, a drawing of the target VTA from a user.

4. The method of claim 2, wherein determining the estimated VTA comprises determining the estimated VTA so that the estimated VTA closely matches the target VTA.

5. The method of claim 4, wherein determining the estimated VTA to closely match the target VTA comprises determining the estimated VTA so that the estimated VTA does not extend beyond a perimeter of the target VTA.

6. The method of claim 1, further comprising displaying the estimated VTA overlaid on a representation of a brain and the leadwire.

7. The method of claim 1, further comprising conducting at least one cognitive function test or motor function test during or after the stimulation.

8. The method of claim 7, further comprising modifying the set of stimulation parameters based on results of the at least one cognitive function test or motor function test.

9. The method of claim 8, wherein the results are used for modification of stimulation parameters to reduce creep of current to non-motor anatomic regions.

10. The method of claim 8, wherein the at least one cognitive function test or motor function test comprises an n-back test.

11. The method of claim 8, wherein the at least one cognitive function test or motor function test is a force-maintenance task.

12. The method of claim 1, wherein the estimated VTA comprises less than 10% of the globus pallidus.

13. A system for treating a neurological disorder that results in abnormal motor function, the system comprising:
    a deep brain stimulation device configured and arranged for implantation in a patient and for providing electrical stimulation to the patient, the deep brain stimulation device comprising a leadwire and electrodes disposed along the leadwire; and
    a computer processor configured and arranged to perform actions, the actions comprising;
        determine an estimated volume of tissue activated (VTA) using a set of stimulation parameters, wherein the estimated VTA comprises at least a portion of at least one of the zona incerta, lenticular fasciculus, or motor region of a globus pallidus and the estimated VTA comprises less than 10% of non-motor anatomical-neural regions of a subthalamic nucleus; and
        provide the set of stimulation parameters to the deep brain stimulation device for stimulating the portion of the at least one of the zona incerta, lenticular fasciculus, or motor region of the globus pallidus using the deep brain stimulation device and the set of stimulation parameters.

14. The system of claim 13, wherein the actions further comprise
    obtain a target volume of tissue activated (VTA), wherein the target VTA comprises less than 10% of the non-motor anatomical-neural regions of the subthalamic nucleus, wherein the target VTA comprises at least a portion of at least one of the zona incerta, lenticular fasciculus, or motor region of the globus pallidus.

15. The system of claim 14, wherein the action of obtain the target VTA comprises receive a drawing of the target VTA from a user.

16. The system of claim 14, wherein the action of determine the estimated VTA comprises determine the estimated VTA so that the estimated VTA closely matches the target VTA.

17. The system of claim 16, wherein the action of determine the estimated VTA to closely match the target VTA comprises determine the estimated VTA so that the estimated VTA does not extend beyond a perimeter of the target VTA.

18. The system of claim 13, wherein the system further comprises a display coupled to the computer processor and the actions further comprise display, on the display, the estimated VTA overlaid on a representation of a brain and the leadwire.

19. The system of claim 13, wherein the actions further comprise conduct at least one cognitive function test or motor function test during or after the stimulation.

20. A system for treating a neurological disorder that results in abnormal motor function, the system comprising:

a deep brain stimulation device configured and arranged for implantation in a patient and for providing electrical stimulation to the patient, the deep brain stimulation device comprising a leadwire and electrodes disposed along the leadwire; and a computer processor configured and arranged to perform actions, the actions comprising;

determine an estimated volume of tissue activated (VTA) using a set of stimulation parameters, wherein the estimated VTA comprises at least a portion of at least one of a zona incerta, a lenticular fasciculus, or motor region of a globus pallidus and the estimated VTA comprises less than 10% of the globus pallidus; and provide the set of stimulation parameters to the deep brain stimulation device for stimulating the portion of the at least one of the zona incerta, lenticular fasciculus, or motor region of the globus pallidus using the deep brain stimulation device and the set of stimulation parameters.

* * * * *